US006567165B1

United States Patent
Tsuchiya et al.

(10) Patent No.: US 6,567,165 B1
(45) Date of Patent: May 20, 2003

(54) CONCENTRATION MEASURING METHOD AND APPARATUS FOR ABSORPTION COMPONENT IN SCATTERING MEDIUM

(75) Inventors: Yutaka Tsuchiya, Hamamatsu (JP); Tsuneyuki Urakami, Hamamatsu (JP)

(73) Assignee: Hamamatsu Photonics K.K., Shizuoka-ken (JP)

( * ) Notice: Subject to any disclaimer, the term of this patent is extended or adjusted under 35 U.S.C. 154(b) by 125 days.

(21) Appl. No.: 09/672,832

(22) Filed: Sep. 29, 2000

Related U.S. Application Data

(63) Continuation-in-part of application No. PCT/JP99/01734, filed on Apr. 1, 1999.

(30) Foreign Application Priority Data

Apr. 2, 1998 (JP) ............................................. 10-090404

(51) Int. Cl.[7] ............................................. G01N 21/00
(52) U.S. Cl. ........................................ 356/338; 356/343
(58) Field of Search ................................ 356/337, 338, 356/341, 342, 343, 433, 436, 441, 442

(56) References Cited

U.S. PATENT DOCUMENTS

| 5,441,054 A | * | 8/1995 | Tsuchiya | .................... | 128/665 |
| 5,983,121 A | * | 11/1999 | Tsuchiya | .................... | 600/310 |
| 6,075,610 A | * | 6/2000 | Ueda et al. | ................. | 356/432 |

FOREIGN PATENT DOCUMENTS

| EP | 0 656 536 A1 | 6/1995 |
| EP | 0 710 832 A1 | 5/1996 |
| JP | 8-94517 | 4/1996 |

OTHER PUBLICATIONS

Japanese Journal of Applied Physics, vol. 34, No. 1A, (Japan), The Japan Society of Applied Physics and the Physical Society of Japan, (Jan. 1, 1995), pp. L79–81.
Japanese Journal of Applied Physics, vol. 37, No. 5A, (Japan), The Japan Society of Applied Physics and the Physical Society of Japan, (May 15, 1998), pp. 2717–2723.
Hikari Allience, vol. 9, No. 11, (Japan), Nippon Kogyo Shuppan, 11/98, pp. 6–8.

* cited by examiner

*Primary Examiner*—Michael P. Stafira

(57) ABSTRACT

A concentration measuring apparatus for an absorption component in a scattering medium includes a light source (2) for generating at least two light rays having predetermined wavelengths, the light rays having different transport scattering coefficients for a scattering medium (20) as an object to be measured, and a known ratio of the transport scattering coefficients; light incidence means (6) for making the light rays incident from a light incident position into the scattering medium (20); photodetection means (12), (13) for detecting the light ray which has propagated inside the scattering medium (20) at at least one photodetection position different from the light incident position to acquire at least one photodetection signal; parameter detection means (15) for detecting, on the basis of the photodetection signal, a light intensity and a mean flight pathlength at the light detection position for each of the at least two light rays having predetermined wavelengths; and arithmetic processing means (16) for calculating a concentration of an absorption component on the basis of a predetermined relationship between the ratio of the transport scattering coefficients, the light intensity, the mean flight pathlength, and a difference between absorption coefficients per unit concentration of the absorption component for the at least two light rays having predetermined wavelengths.

22 Claims, 12 Drawing Sheets

NEAR-INFRARED ABSORPTION SPECTRUM
OF Hb(0.37mM) AND Mb(0.15mM)

ABSOLUTE SPECTRUM
SOLID LINE : OXYGENATED
DOTTED LINE : DEOXYGENATED

CONCENTRATION MEASURING METHOD AND APPARATUS FOR ABSORPTION COMPONENT IN SCATTERING MEDIUM

RELATED APPLICATION

The present application is a continuation-in-part application of PCT application No. PCT/JP99/01734 filed on Apr. 1, 1999, designating U.S.A. and now pending.

BACKGROUND OF THE INVENTION

1. Field of the Invention

The present invention relates to a concentration measuring method and apparatus for an absorption component in a scattering medium. More specifically, the present invention relates to a concentration measuring method and apparatus for an absorption component in a scattering medium, in which at least two light rays with predetermined wavelengths, whose scattering coefficients are different and have a known ratio, are made incident on a scattering medium such as living bodies having various shapes, light which has a predetermined wavelength and diffuses and propagates inside the scattering medium and comes to the surface is detected to obtain the light intensity and mean flight pathlength (mean optical pathlength) at the detection position, and on the basis of the light intensity and mean flight pathlength, a relative value or an absolute value of concentration of a specific absorption component in the scattering medium, oxygen saturation of hemoglobin, and a change in time or a spatial distribution thereof can be highly accurately and noninvasively measured without any influence of the shape of the scattering medium.

2. Related Background Art

There is a strong demand for highly accurate and noninvasive measurement of a relative value and an absolute value of concentration of a specific absorption component in a scattering medium such as a living body, and a change in time as well as a spatial distribution thereof. Various methods or examinations have been used or made so far, including a method using continuous light (CW light) or modulated light (e.g., pulse light, rectangular waveform light, or sine-wave-modulated light) and a method using light components with different wavelengths.

In these conventional techniques, a method and apparatus for sufficiently accurately measuring the concentration of a specific absorption component in an object such as living bodies whose regions have different shapes or shapes have individual differences even in identical regions have not been developed yet. This poses a serious problem in noninvasive measurement of a living body using light, and a strong demand has arisen for improvement thereof.

Light incident on a scattering medium such as a living body diffuses and propagates inside the scattering medium while being scattered and absorbed, and partially comes to the surface. Since the scattering medium is normally surrounded by air, the light coming to the surface dissipates through the free space.

In the measurement of internal information of a scattering medium, light that has come to the surface in the above way is detected. In this case, if the boundary condition (shape) of the scattering medium changes, e.g., depending on whether the scattering medium has a spherical shape or a rectangular parallelopiped shape, the intensity and behavior of light coming to a predetermined position of the surface changes greatly.

Hence, to increase the accuracy of such measurement, the behavior of light in the scattering medium must be understood well. As is recently known, the behavior of light in a scattering medium can be relatively accurately described and analyzed by analysis, experiments, and examinations of Monte Carlo simulation using a computer, or photon diffusion theory.

As described above, to understand the behavior of light in a scattering medium, Monte Carlo simulation or photon diffusion theory is conventionally used. However, Monte Carlo simulation takes a verylong time for calculation and cannot calculate the concentration of a specific absorption component in a scattering medium from the result of simulation.

To use the photon diffusion theory, a boundary condition must be set to actually solve a photon diffusion equation. However, the boundary condition largely depends on the shape of a scattering medium. For this reason, for accurate measurement, a new boundary condition must be set to solve a photon diffusion equation every time the shape of the scattering medium changes. Additionally, a relatively accurate boundary condition can be set for only a scattering medium with a very simple shape, such as an infinite space, semi-infinite space, infinite circular cylinder, or infinitely spreading slab having a limited thickness. As a result, to measure a living body having a complex shape using the photon diffusion theory, it is indispensable to use an approximate boundary condition, resulting in a large measurement error.

As a solution to these problems, the present inventor has already developed and filed a patent application (Japanese Patent Application Laid-Open Gazette No. Hei 8-94517) for a method of measuring the absorption coefficient of a scattering material and the concentration of an absorber on the basis of the Micro-Beer-Lambert law.

SUMMARY OF THE INVENTION

The method in Japanese Patent Application Laid-Open Gazette No. Hei 8-94517 is excellent because it can quantitatively measure an absorption coefficient independently of the boundary condition (shape) of an object to be measured. However, this method uses a plurality of light components with different wavelengths whose scattering characteristics are equal or can be regarded to be equal for a scattering medium to be measured. Hence, the method disclosed in Japanese Patent Application Laid-Open Gazette No. Hei 8-94517 is not satisfactory because it can use only limited wavelengths, and as the difference in scattering characteristics between the plurality of wavelengths of light components in use increases, the measurement error increases, or if the difference further increases, measurement is disabled.

As described above, a diffused light handling method which can be systematically applied, without any limitation on usable wavelengths, to a scattering medium having scattering characteristics depending on a wavelength and a different boundary condition has not been developed yet. For this reason, it is conventionally impossible to systematically accurately measure the concentration of an internal specific absorption component in such a scattering medium without limiting a wavelength to be used.

The present invention has been made to solve the above problems of the prior art, and has as its object to provide a concentration measuring method and apparatus for an absorption component in a scattering medium, in which the basic relationship associated with the behavior of light in a scattering medium having scattering characteristics depending on a wavelength and having a different boundary condition is newly disclosed, even when the scattering characteristics depend on the wavelength, a relative value or an absolute value of concentration of a specific absorption component in scattering media having various shapes can be accurately measured using that relationship without any limitation on the wavelength to be used and any influence of the wavelength dependence of such scattering characteristics, and a change in time or a spatial distribution thereof can also be accurately measured without any influence of the wavelength dependence of the scattering characteristics.

In the present invention, at least two light rays having predetermined wavelengths and a known ratio of transport scattering coefficients are made incident on a scattering medium having various boundary conditions (shapes), a light intensity and mean flight pathlength of each light ray having the predetermined wavelength at the light detection position are obtained, and on the basis of these values, a relative value or an absolute value of concentration of a specific absorption component are obtained by arithmetic processing without any influence of the boundary condition of the scattering medium or wavelength dependence of scattering characteristics.

Specifically, a concentration measuring method for an absorption component in a scattering medium according to the present invention comprises (a) a light generation step of generating at least two light rays having predetermined wavelengths (light rays having wavelengths of two types or more), the light rays having different transport scattering coefficients for a scattering medium as an object to be measured, and a known ratio of the transport scattering coefficients, (b) a light incidence step of making the light rays incident from a light incident position into the scattering medium, (c) a photodetection step of detecting the light ray which has propagated inside the scattering medium at at least one photodetection position different from the-light incident position to acquire at least one photodetection signal, (d) a parameter detection step of detecting, on the basis of the photodetection signal, a light intensity and a mean flight pathlength at the light detection position for each of the at least two light rays having predetermined wavelengths, and (e) an arithmetic processing step of calculating a concentration of an absorption component on the basis of a predetermined relationship between the ratio of the transport scattering coefficients, the light intensity, the mean flight pathlength, and a difference between absorption coefficients per unit concentration of the absorption component for the at least two light rays having predetermined wavelengths.

A concentration measuring apparatus for an absorption component in a scattering medium according to the present invention comprises (a) a light source for generating at least two light rays having predetermined wavelengths (light rays having wavelengths of two types or more), the light rays having different transport scattering coefficients for a scattering medium as an object to be measured, and a known ratio of the transport scattering coefficients, (b) light incidence means for making the light rays incident from a light incident position into the scattering medium, (c) photodetection means for detecting the light ray which has propagated inside the scattering medium at at least one photodetection position different from the light incident position to acquire at least one photodetection signal, (d) parameter detection means for detecting, on the basis of the photodetection signal, a light intensity and a mean flight pathlength at the light detection position for each of the at least two light rays having predetermined wavelengths, and (e) arithmetic processing means for calculating a concentration of an absorption component on the basis of a predetermined relationship between the ratio of the transport scattering coefficients, the light intensity, the mean flight pathlength, and a difference between absorption coefficients per unit concentration of the absorption component for the at least two light rays having predetermined wavelengths.

In the method and apparatus of the present invention, each of the at least two light rays having predetermined wavelengths may be a pulse light ray.

Each of the at least two light rays having predetermined wavelengths may be a sine-wave-modulated light ray having a predetermined modulation frequency component, the light intensity may be calculated from (i) a DC component of the photodetection signal or (ii) an amplitude of a signal having the predetermined modulation frequency component, which is contained in the photodetection signal, and the mean flight pathlength may be calculated from a phase delay of the signal having the predetermined modulation frequency component.

Each of the at least two light rays having predetermined wavelengths may be a modulated light ray having a predetermined repetitive modulation frequency component, the light intensity may be calculated from (i) a DC component of the photodetection signal or (ii) an amplitude of a signal having the predetermined repetitive modulation frequency component or a frequency component of an integer multiple thereof, which is contained in the photodetection signal, and the mean flight pathlength may be calculated from a phase delay of the signal having the predetermined repetitive modulation frequency component or the frequency component of an integer multiple thereof.

The predetermined relationship between the ratio of the transport scattering coefficients, the light intensity, the mean flight pathlength, and the difference between the absorption coefficients per unit concentration of the absorption component for the at least two light rays having predetermined wavelengths is preferably a relationship derived on the basis of a fact that a value obtained by partially differentiating a natural logarithm of the detected light intensity by the absorption coefficient equals the mean flight pathlength without neglecting a difference in mean flight pathlength due to the difference in scattering coefficient.

In the method and apparatus according to one aspect of the present invention, in the arithmetic processing step (arithmetic processing means), the concentration of the absorption component in the scattering medium is preferably calculated on the basis of a relationship represented by $$V = \ln\frac{I_1(\lambda_1)B_2}{kI_1(\lambda_2)B_1}[(\varepsilon_2 - \varepsilon_1)\{p\langle L_1(\lambda_2)\rangle +$$

$$(1-p)\sqrt{k}\,\langle L_1(\lambda_1)\rangle\} -$$

$$\varepsilon_1(1-\sqrt{k})\langle L_1(\lambda_1)\rangle]^{-1}$$

where
V is the concentration of the absorption component,
$\epsilon_1$ is an absorption coefficient per unit concentration of the absorption component for light having a wavelength $\lambda_1$,
$\epsilon_2$ is an absorption coefficient per unit concentration of the absorption component for light having a wavelength $\epsilon_2$,
$\langle L_1(\lambda_1)\rangle$ is a mean flight pathlength for the light having the wavelength $\lambda_1$,
$\langle L_1(\lambda_2)\rangle$ is a mean flight pathlength for the light having the wavelength $A_2$,
$I_1(\lambda_1)$ is a detected light intensity for light having an incident light intensity $B_1$ and the wavelength $\lambda_1$,
$I_1(\lambda_2)$ is a detected light intensity for light having an incident light intensity $B_2$ and the wavelength $\lambda_2$,
k is a ratio ($\mu_{s2}'/\mu_{s1}'$) of a transport scattering coefficient $\mu_{s2}'$ for the light having the wavelength $\lambda_2$ to a transport scattering coefficient $\mu_{s1}'$ for the light having the wavelength $\lambda_1$, and
p is a predetermined value satisfying $0 \leq p \leq 1$.

In the method and apparatus according to another aspect of the present invention, in the arithmetic processing step (arithmetic processing means), the concentration of the absorption component in the scattering medium is preferably calculated on the basis of a relationship represented by $$V = \ln\frac{I_2(\lambda_1)I_1(\lambda_2)}{I_2(\lambda_2)I_1(\lambda_1)} \times [(\varepsilon_2 - \varepsilon_1)\{p\langle L_2(\lambda_2)\rangle +$$
$$(1-p)\sqrt{k}\langle L_2(\lambda_1)\rangle\} - (\varepsilon_2 - \varepsilon_1)\{q\langle L_1(\lambda_2)\rangle +$$
$$(1-q)\sqrt{k}\langle L_1(\lambda_1)\rangle\} - \varepsilon_1(1 - \sqrt{k})\{\langle L_2(\lambda_1)\rangle +$$
$$\langle L_1(\lambda_1)\rangle\}]^{-1}$$

where
V is the concentration of the absorption component,
$\epsilon_1$ is an absorption coefficient per unit concentration of the absorption component for light having a wavelength $\lambda_1$,
$\epsilon_2$ is an absorption coefficient per unit concentration of the absorption component for light having a wavelength $\lambda_2$,
$\langle L_1(\lambda_1)\rangle$ is a mean flight pathlength at a photodetection position $r_1$ for the light having the wavelength $\lambda_1$,
$\langle L_1(\lambda_2)\rangle$ is a mean flight pathlength at the photodetection position $r_1$ for the light having the wavelength $\lambda_2$,
$\langle L_2(\lambda_1)\rangle$ is a mean flight pathlength at a photodetection position $r_2$ for the light having the wavelength $\lambda_1$,
$\langle L_2(\lambda_2)\rangle$ is a mean flight pathlength at the photodetection position $r_2$ for the light having the wavelength $\lambda_2$,
$I_1(\lambda_1)$ is a detected light intensity at the photodetection position $r_1$ for light having an incident light intensity $B_1$ and the wavelength $\lambda_1$,
$I_1(\lambda_2)$ is a detected light intensity at the photodetection position $r_1$ for light having an incident light intensity $B_2$ and the wavelength $\lambda_2$,
$I_2(\lambda_1)$ is a detected light intensity at the photodetection position $r_2$ for the light having the incident light intensity $B_1$ and the wavelength $\lambda_1$,
$I_2(\lambda_2)$ is a detected light intensity at the photodetection position $r_2$ for the light having the incident light intensity $B_2$ and the wavelength $\lambda_2$,
k is a ratio ($\mu_{s2}'/\mu_{s1}'$) of a transport scattering coefficient $\mu_{s2}'$ for the light having the wavelength $\lambda_2$ to a transport scattering coefficient $\mu_{s1}'$ for the light having the wavelength $\lambda_1$,
p is a predetermined value satisfying $0 \leq p \leq 1$, and
q is a predetermined value satisfying $0 \leq q \leq 1$.

In the present invention, "transport scattering coefficients are different from each other" means that the difference between the transport scattering coefficients for each of at least two light rays having predetermined wavelengths for the scattering medium as a target measurement object is so large that it cannot be neglected.

In the present invention, the concentration of a specific absorption component is calculated on the basis of the basic relationship that holds for various scattering media having scattering characteristics depending on wavelengths and different boundary conditions, i.e., the relationship between the light intensity at the photodetection position, mean flight pathlength, and the difference or ratio between the absorption coefficients per unit concentration of the absorption component for the at least two light rays having predetermined wavelengths, and the value or ratio of the transport scattering coefficients of the scattering component for the at least two light rays having predetermined wavelengths. For this reason, the concentration of the specific absorption component can be more accurately measured without any limitation on the wavelength to be used and any influence of the boundary condition (shape) of the scattering medium. In addition, the change in time or spatial distribution of the concentration of the specific absorption component can also be measured.

In the present invention, the light intensity and mean flight pathlength obtained from actual measurement values are used as parameters for arithmetic processing of the concentration of the specific absorption component. These parameters are obtained using almost all light beams obtained at the photodetection position, i.e., have integrated values. Hence, a high signal-to-noise ratio can be obtained, and consequently, high measurement accuracy can be obtained.

In the present invention, measurement is performed by making at least two light rays having predetermined wavelengths, which have different transport scattering coefficients and a known ratio thereof, incident on a scattering medium. The difference between absorption coefficients of an absorption component for a predetermined wavelength is obtained from measurement values, and the concentration of a specific absorption component is obtained from this difference.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Principle of Invention

The principle of the present invention will be described first. The finding to be described below is disclosed by the present inventors for the first time.

Assume that a scattering medium has a uniform structure, and light emitted from a light source arranged on the surface of the scattering medium propagates inside the scattering medium and is detected by a photodetector placed on the surface. In this case, the scattering medium can have an arbitrary shape as far as it is comprised of surfaces which disable re-incidence of diffused light.

Figure 1:
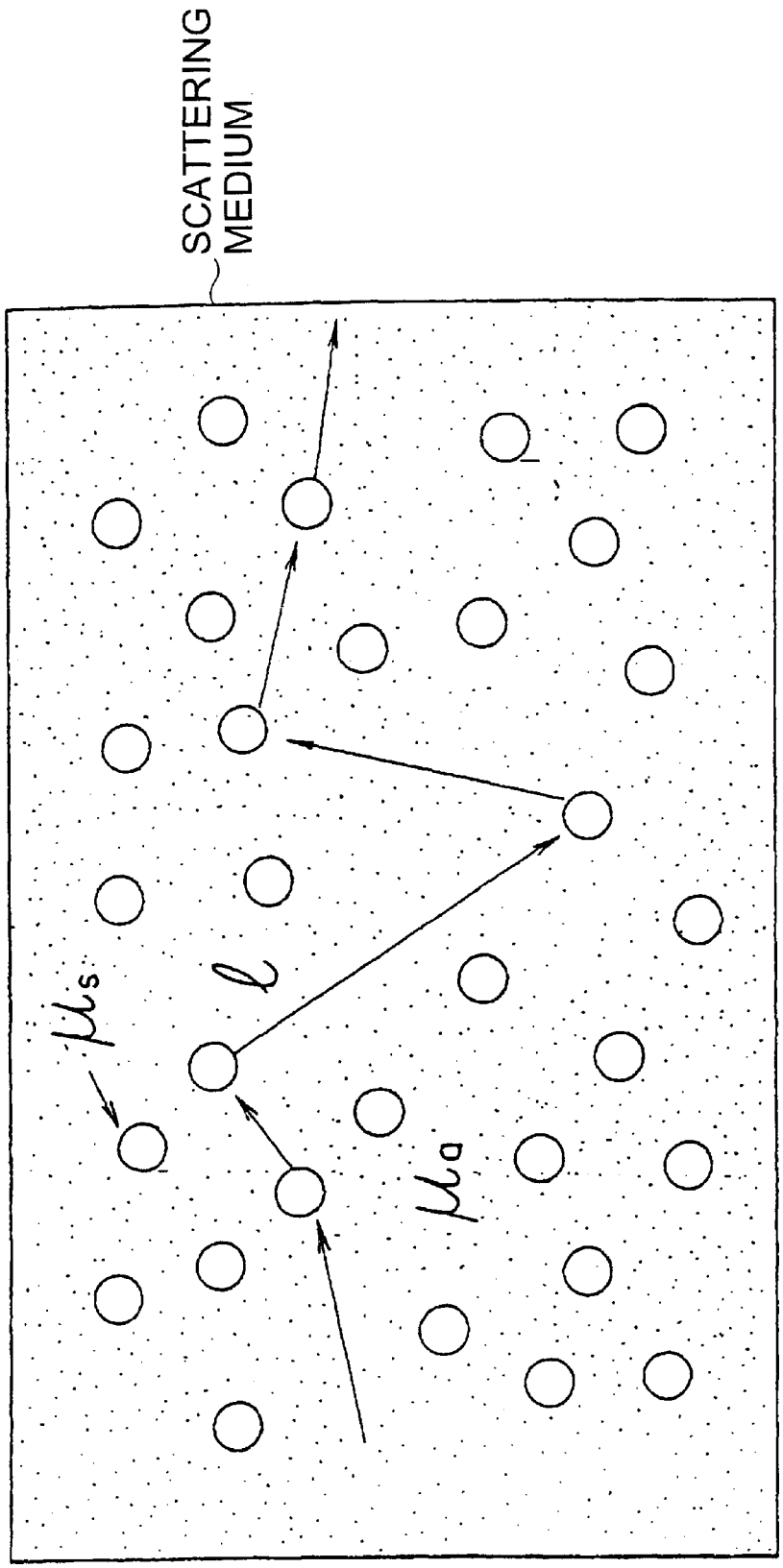
FIG. 1 is a schematic view of the track of light that has propagated inside a scattering medium.

FIG. 1 shows an example of a track of detected light (or photon) which has propagated inside the scattering medium.

The light is scattered by scattering particles, so the optical path zigzags. At this time, the Lambert-Beer law holds for a zigzag flight distance l. The intensity of propagation light exponentially attenuates with respect to the zigzag flight distance (accumulated distance) l. Letting c be the velocity of light in the medium, and t be the time-of-flight, the flight distance is given by l=ct.

Figure 2:
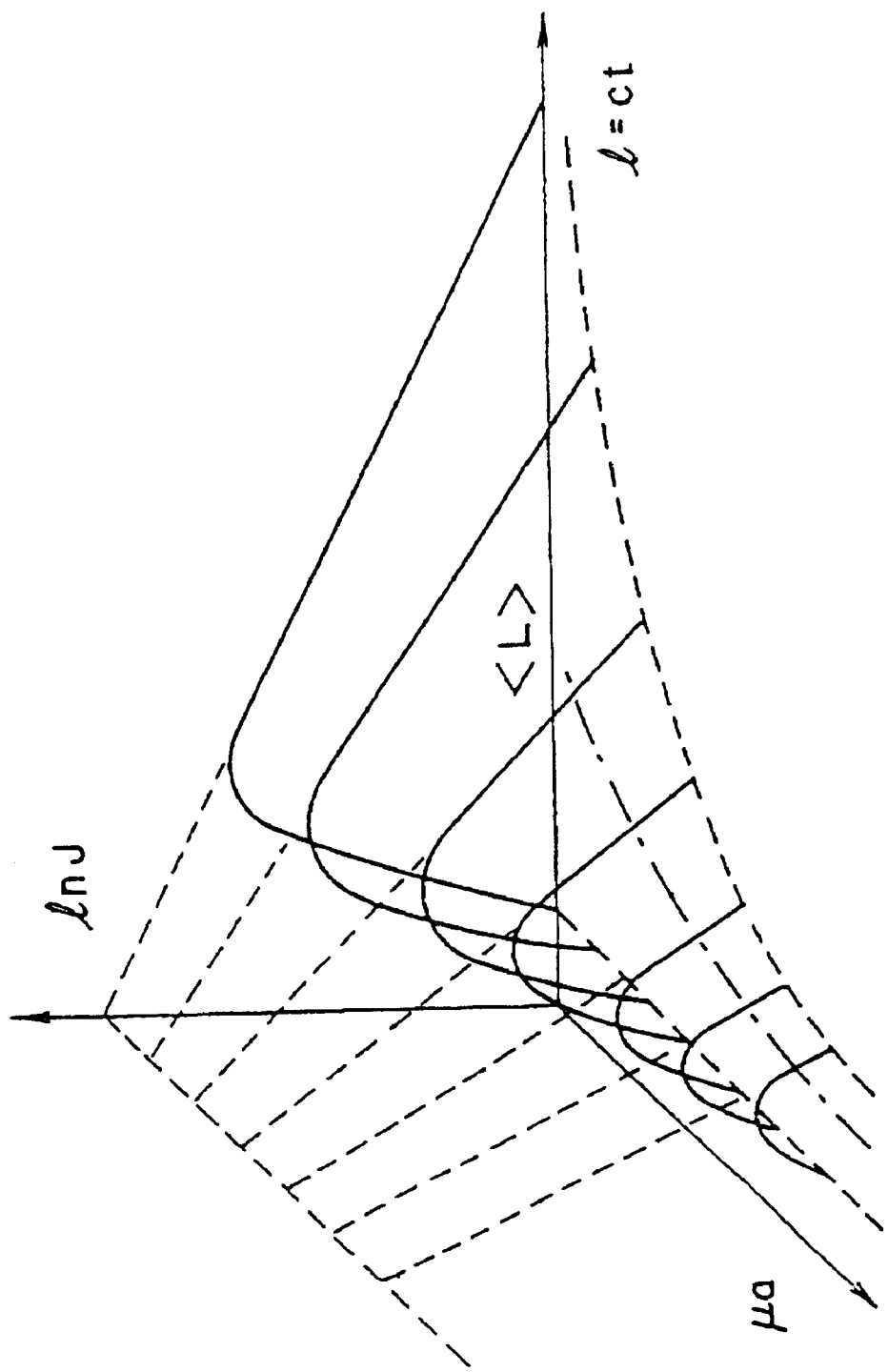
FIG. 2 is a schematic view showing an example of a time-resolved measurement waveform.

On the other hand, consider a time waveform J (ct) of a photodetection signal obtained by time-resolved measurement. As shown in FIG. 2, the flight distance l corresponds to ct=l on the abscissa of the time waveform J (ct) of the photodetection signal.

The following important expressions associated with the flight distance and absorption of zigzag light detected at time t are obtained. As is apparent, the degree of absorption is associated with only the flight distance l and scattering characteristics $\mu_a$. That is $$ct = l = nl_s = n/\mu_s \tag{1}$$

$$J(ct) = B_0 A(\mu_s, t)[\exp(-\mu_a/\mu_s)]^n \tag{2}$$

$$= B_0 A(\mu_s, t)\exp(-\mu_a l)$$

$$= B_0 A(\mu_s, t)\exp(-\mu_a ct)$$

where
- $l_s$ is the average free flight distance $l_s = 1/\mu_s$,
- n is the number of times of collision with scattering particles
- $\mu_a$ is the absorption coefficient,
- $\mu_s$ is the scattering coefficient,
- $B_0$ is the incidence intensity of light incident on the scattering medium, and
- $B_0 A(\mu_s,t)$ is the photodetection signal when absorption does not occur (when $\mu_a=0$). In this case, $l \gg l_s$, and $A(\mu_s,t)$ represents the influence of scattering.

Basic expressions associated with the behavior of light in the scattering medium are obtained from the above relationships. Equations associated with the time waveform (corresponding to time-resolved measurement) are $$J(\mu_s,\mu_a,t) = B_0 A(\mu_s,t)\exp(-\mu_a ct) \tag{3}$$

$$\ln[J(\mu_s,\mu_a,t)] = -\mu_a ct + \ln[B_0 A(\mu_s,t)] \tag{4}$$

$$\frac{\partial}{\partial \mu_a} J(\mu_s, \mu_a, t) = -ct B_0 A(\mu_s, t)\exp(-\mu_a ct) \tag{5}$$

$$\frac{\partial}{\partial \mu_a} \ln[J(\mu_s, \mu_a, t)] = -ct \tag{6}$$

Equation (3) is obtained by rewriting equation (2).

Equation (3) or (4) of the above four equations is suitable for quantitatively calculating the hemoglobin concentration of a living body.

Since a detected light intensity I is obtained by time-integrating $J(\mu_s,\mu_a,t)$, the following basic expressions are obtained in association with the detected light intensity I (time-integrated value, corresponding to CW measurement). Laplace transform ($s=c\mu_a$) of $A(\mu_s,t)$ is represented by $F[A(\mu_s,t)]$.

$$I(\mu_s, \mu_a) = B_0 \int_0^\infty A(\mu_s, t)\exp(-\mu_a ct)\, dt \tag{7}$$

$$= B_0 F[A(\mu_s, t)]$$

$$\ln I(\mu_s, \mu_a) = \ln B_0 + \ln[F[A(\mu_s, t)]] \tag{8}$$

$$\frac{\partial}{\partial \mu_a} I(\mu_s, \mu_a) = -B_0 c F[tA(\mu_s, t)] \tag{9}$$

$$\frac{\partial}{\partial \mu_a} \ln I(\mu_s, \mu_a) = -\frac{cF[tA(\mu_s, t)]}{F[A(\mu_s, t)]} \tag{10}$$

$$= -c\langle t \rangle = -\langle L(\mu_s, \mu_a)\rangle$$

$\langle L(\mu_s,\mu_a)\rangle$ in equation (10) equals the weighted average $c\langle t \rangle$ of the distribution of $J(\mu_s,\mu_a,t)$ in equation (3) and is called a barycenter, mean flight pathlength, or mean optical pathlength.

This mean flight pathlength $\langle L(\mu_s,\mu_a)\rangle$ can be calculated by calculating the time-revolved waveform $J(\mu_s,\mu_a,t)$ of the detection signal. This can also be calculated by another method, e.g., on the basis of a phase delay of the photodetection signal with respect to modulated light incidence. Since the mean flight pathlength $\langle L(\mu_s,\mu_a)\rangle$ is an amount obtained using the entire photodetection signal, i.e., an integrated amount, a high signal-to-noise ratio (S/N) is obtained. Note that the mean flight pathlength $\langle L(\mu_s,\mu_a)\rangle$ generally depends on $\mu_a$.

The above result has also been confirmed by Monte Carlo simulation. The above result also reveals that, when using a photon diffusion equation, it is appropriate to define and use a new diffusion constant D obtained by removing the absorption coefficient from the conventional diffusion constant. That is, $$D = \frac{1}{3\mu'_s} = \frac{1}{3(1-g)\mu_s} \quad (11)$$

where $\mu_s'$ is a transport scattering coefficient $\mu_s'=(1-g)\mu_s$ by similar principle (where g is the average value of the cosine of the scattering angle).

In the present invention, the following analysis is executed in consideration of the wavelength dependence of the scattering coefficient. First, both the left and right-hand sides of equation (10) are integrated from 0 to $\mu_a$ to obtain $$\ln I(\mu_s, \mu_a) = -\int_0^{\mu_a} \langle L(\mu_s, \mu_a)\rangle d\mu_a + \ln B_0 + \int_0^\infty s(\mu_s, t) dt \quad (12)$$
$$\approx -G(\mu_a) + \ln B_0 + \int_0^\infty s(\mu_s, t) dt$$

In equation (12), $$G(\mu_a) = \int_0^{\mu_a} \langle L(\mu_s, \mu_a)\rangle d\mu_a \quad (13)$$

Assume that the scattering medium contains one type of absorption component. Let $\epsilon_1$ and $\epsilon_2$ be the absorption coefficients per unit concentration of the absorption component with respect to light components having wavelengths $\lambda_1$ and $\lambda_2$ respectively. A concentration of the absorption components is given by $$V(\epsilon_1 - \epsilon_2) = \mu_{a1} - \mu_{a2} \quad (14)$$

where $\mu_{a1}$ and $\mu_{a2}$ are the absorption coefficients of the absorption component at the wavelengths $\lambda_1$ and $\lambda_2$, respectively.

Hence, when the mean flight pathlengths $<L(\lambda_1)>=<L_1(\mu_{s1},\mu_{a1})>$ and $<L(\lambda_2)>=<L_1(\mu_{s2},\mu_{a2})>$ and light intensities $I_1(\lambda_1)=I_1(\mu_{s1},\mu_{a1})$ and $I_1(\lambda_2)=I_1(\mu_{s2},\mu_{a2})$ are to be detected for incident light having the wavelength $\lambda_1$ (incident light intensity $B_1$) and wavelength $\lambda_2$ (incident light intensity $B_2$), $$\ln\frac{I_1(\mu_{s1},\mu_{a1})}{I_1(\mu_{s2},\mu_{a2})} = G_1(\mu_{a2}) - G_1(\mu_{a1}) + \ln\frac{B_1}{B_2} + \ln\frac{\int_0^\infty s(\mu_{s1},t)dt}{\int_0^\infty s(\mu_{s2},t)dt} \quad (15)$$
$$= \int_0^{\mu_{a2}}\langle L_1(\mu_{s2},\mu_a)\rangle d\mu_a - \int_0^{\mu_{a1}}\langle L_1(\mu_{s1},\mu_a)\rangle d\mu_a +$$
$$\ln\frac{B_1}{B_2} + \ln k$$
$$= \int_{\mu_{a1}}^{\mu_{a2}}\langle L_1(\mu_{s2},\mu_a)\rangle d\mu_a - \int_0^{\mu_{a1}}[\langle L_1(\mu_{s1},\mu_a)\rangle -$$
$$\langle L_1(\mu_{s2},\mu_a)\rangle] d\mu_a + \ln\frac{B_1}{B_2} + \ln k$$

In equation (15), $$\ln\frac{\int_0^\infty s(\mu_{s1},t)dt}{\int_0^\infty s(\mu_{s2},t)dt} = \ln\frac{\mu'_{s2}}{\mu'_{s1}} = k$$

Equation (15) can be rewritten into $$\ln\frac{I_1(\mu_{s1},\mu_{a1})B_2}{kI_1(\mu_{s2},\mu_{a2})B_1} = \int_{\mu_{a1}}^{\mu_{a2}}\langle L_1(\mu_{s2},\mu_a)\rangle d\mu_a - \quad (16)$$
$$\int_0^{\mu_{a1}}[\langle L_1(\mu_{s1},\mu_a)\rangle - \langle L_1(\mu_{s2},\mu_a)\rangle] d\mu_a$$

Figure 3:
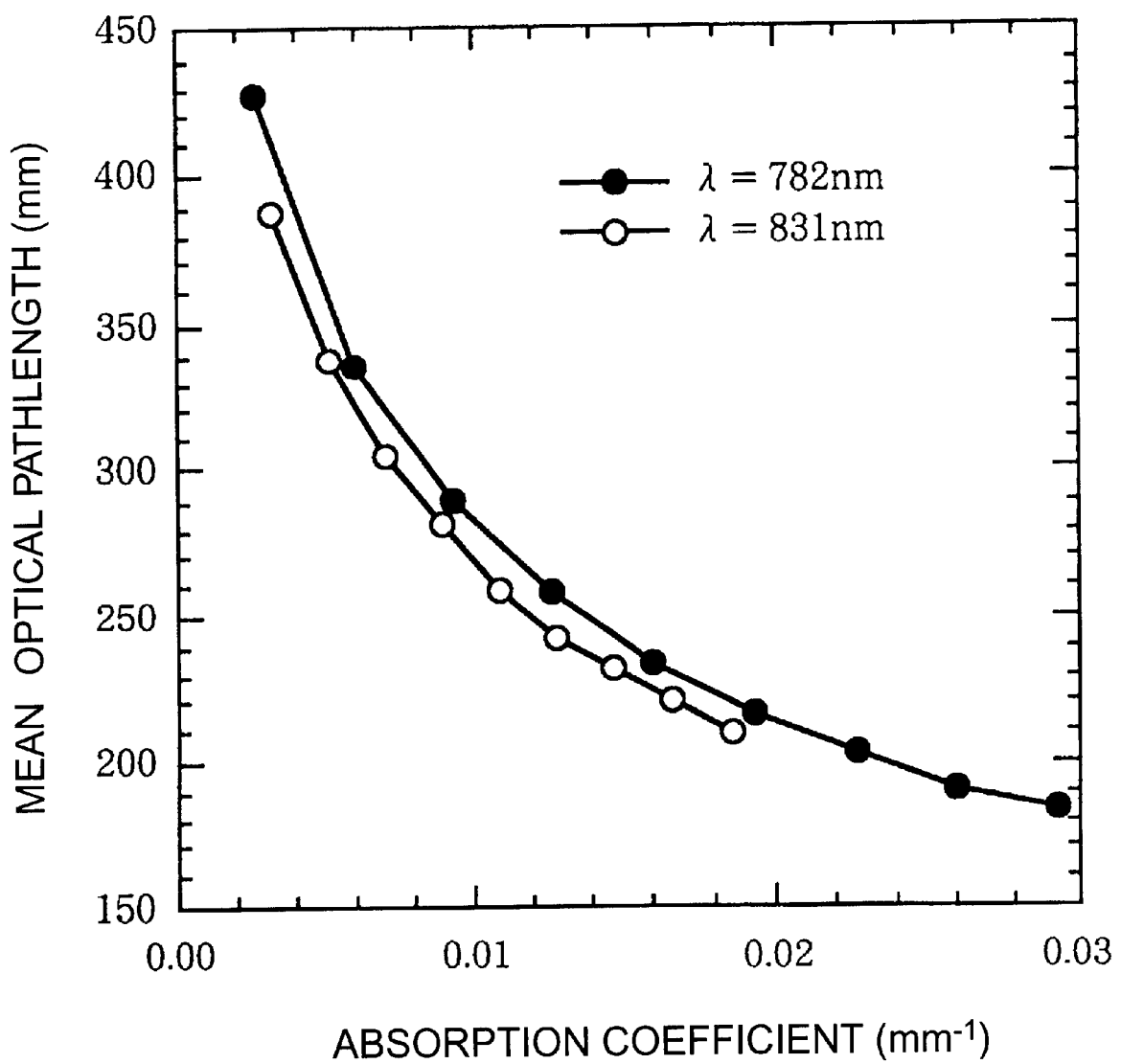
FIG. 3 is a graph showing the relationship between an absorption coefficient and a mean optical pathlength when scattering characteristics have a wavelength dependence.

The present inventors have found that the influence of the difference in scattering coefficient of the second term of the right-hand side of the above equation is neglected in the prior-art application (Japanese Patent Application Laid-Open Gazette No. Hei 8-94517) to result in an analysis error. FIG. 3 shows the result of an experimental examination of the relationship between the absorption coefficient ($\mu_a$) and the mean optical pathlength (L: mean flight pathlength) when the scattering coefficient has a wavelength dependence. Measurement was done using a 1% intralipid solution as a scattering material and greenish brown ink as an absorber. Equation (16) related to the mean optical pathlength is plotted in FIG. 3. More specifically, even when measurement is done for the same absorption coefficient, the mean optical pathlength changes due to the different scattering coefficients.

In the present invention, while correcting this point, the following equations for analysis are obtained.

The mean optical pathlength can also be obtained from a photon diffusion equation. The relationship of the mean optical pathlength is obtained using a photon diffusion equation. Such photon diffusion equation is given by $$\langle L(\mu'_s,\mu_a)\rangle = \frac{3}{2}\mu'_s\frac{r^2}{1+r\mu_{eff}} \quad (17)$$

for semi-infinite space reflection-type and slab transmission-type measurement where $\mu_s'$ is the transport scattering coefficient by similar principle, and $\mu_{eff}$ is given by $$\mu_{eff} = \sqrt{3\mu_a\mu'_s} \quad (18)$$

Assume that $<L(\mu_s,\mu_a)>$ and $<L(\mu_s',\mu_a)>$ equal each other upon conversion of $\mu_s'=(1-g)\mu_s$ (where g is the mean cosine value of scattering angle).

Hence, for $\lambda_1$ and $\lambda_2$, $$\langle L(\mu'_{s1},\mu_a)\rangle = \frac{3}{2}\mu'_{s1}\frac{r^2}{1+r\sqrt{3\mu_a\mu'_{s1}}} \quad (19)$$

$$\langle L(\mu'_{s2},\mu_a)\rangle = \frac{3}{2}\mu'_{s2}\frac{r^2}{1+r\sqrt{3\mu_a\mu'_{s2}}} \quad (20)$$

hold. Hence, $$\frac{\langle L(\mu'_{s1},\mu_a)\rangle}{\langle L(\mu'_{s2},\mu_a)\rangle} = \frac{\mu'_{s1}}{\mu'_{s2}}\frac{1+r\sqrt{3\mu_a\mu'_{s2}}}{1+r\sqrt{3\mu_a\mu'_{s1}}} \quad (21)$$

One of the following approximate equations $$\frac{\langle L(\mu'_{s1}, \mu_a)\rangle}{\langle L(\mu'_{s2}, \mu_a)\rangle} = \sqrt{\frac{\mu'_{s1}}{\mu'_{s2}}} \quad \cdots \quad 1 \ll r\sqrt{3\mu_a\mu'_{s1}},\ 1 \ll r\sqrt{3\mu_a\mu'_{s2}} \quad (22)$$

$$\frac{\langle L(\mu'_{s1}, \mu_a)\rangle}{\langle L(\mu'_{s2}, \mu_a)\rangle} = \frac{\mu'_{s1}}{\mu'_{s2}} \quad \cdots \quad 1 \gg r\sqrt{3\mu_a\mu'_{s1}},\ 1 \gg r\sqrt{3\mu_a\mu'_{s2}} \quad (23)$$

holds. Normally, r>5 mm. For a parameter of a living body, equation (22) is satisfied. Equation (22) will be considered below. More specifically, in the range where equation (22) holds, $$\langle L(\mu'_{s1}, \mu_a)\rangle = \sqrt{\frac{\mu'_{s1}}{\mu'_{s2}}} \langle L(\mu'_{s2}, \mu_a)\rangle \quad (24)$$

A substitution of equation (24) into equation (16) yields $$\ln\frac{I_1(\mu_{s1}, \mu_{a1})B_2}{kI_1(\mu_{s2}, \mu_{a2})B_1} = \int_{\mu_{a1}}^{\mu_{a2}} \langle L_1(\mu_{s2}, \mu_a)\rangle d\mu_a - \quad (25)$$

$$\int_0^{\mu_{a1}} [\langle L_1(\mu_{s1}, \mu_a)\rangle - \langle L_1(\mu_{s2}, \mu_a)\rangle] d\mu_a$$

$$= \int_{\mu_{a1}}^{\mu_{a2}} \langle L_1(\mu_{s2}, \mu_a)\rangle d\mu_a -$$

$$\int_0^{\mu_{a1}} \left(\sqrt{\frac{\mu'_{s1}}{\mu'_{s2}}} - 1\right) \langle L_1(\mu_{s2}, \mu_a)\rangle] d\mu_a$$

When the mean value theorem is used in the first term of the right-hand side of equation (25), $\mu_{ax}$ that satisfies $$\int_{\mu_{a1}}^{\mu_{a2}} \langle L_1(\mu_{s2}, \mu_a)\rangle d\mu_a = (\mu_{a2} - \mu_{a1})\langle L_1(\mu_{s2}, \mu_{ax})\rangle \quad (26)$$

is present. In this case, $\mu_{a1} \leq \mu_{ax} \leq \mu_{a2}$ or $\mu_{a2} \leq \mu_{ax} \leq \mu_{a1}$. Equation (26) can also be represented using appropriate p satisfying $0 \leq p \leq 1$ $$\int_{\mu_{a1}}^{\mu_{a2}} \langle L_1(\mu_{s2}, \mu_a)\rangle d\mu_a = (\mu_{a2} - \mu_{a1})\langle L_1(\mu_{s2}, \mu_{ax})\rangle = \quad (27)$$

$$(\mu_{a2} - \mu_{a1})[p\langle L_1(\mu_{s2}, \mu_{a2})\rangle + (1-p)\langle L_1(\mu_{s2}, \mu_{a1})\rangle] =$$

$$(\mu_{a2} - \mu_{a1})\left[p\langle L_1(\mu_{s2}, \mu_{a2})\rangle + (1-p)\sqrt{\frac{\mu'_{s2}}{\mu'_{s1}}} \langle L_1(\mu_{s1}, \mu_{a1})\rangle\right] =$$

$$(\mu_{a2} - \mu_{a1})[p\langle L_1(\mu_{s2}, \mu_{a2})\rangle + (1-p)\sqrt{k}\langle L_1(\mu_{s1}, \mu_{a1})\rangle]$$

If equation (24) holds until $\mu_a=0$, the second term of the right-hand side of equation (25) can be rewritten to $$-\mu_{a1}\left(\sqrt{\frac{\mu'_{s1}}{\mu'_{s2}}} - 1\right)\langle L_1(\mu_{s2}, \mu_a)\rangle = \quad (28)$$

$$-\mu_{a1}\left(\sqrt{\frac{\mu'_{s1}}{\mu'_{s2}}} - 1\right)\langle L_1(\mu_{s1}, \mu_a)\rangle \sqrt{\frac{\mu'_{s2}}{\mu'_{s1}}} =$$

$$-\mu_{a1}\left(1 - \sqrt{\frac{\mu'_{s2}}{\mu'_{s1}}}\right)\langle L_1(\mu_{s1}, \mu_a)\rangle = -\mu_{a1}(1 - \sqrt{k})\langle L_1(\mu_{s1}, \mu_a)\rangle$$

Hence, substitutions of equations (27) and (28) into equation (25) yield $$\ln\frac{I_1(\mu_{s1}, \mu_{a1})B_2}{kI_1(\mu_{s2}, \mu_{a2})B_1} = (\mu_{a2} - \mu_{a1})[p\langle L_1(\mu_{s2}, \mu_{a2})\rangle + \quad (29)$$

$$(1-p)\sqrt{k}\langle L_1(\mu_{s1}, \mu_{a1})\rangle] -$$

$$\mu_{a1}(1-\sqrt{k})\langle L_1(\mu_{s1}, \mu_{a1})\rangle$$

Substitutions of $$\mu_{a1} = V\epsilon_1 \quad (30)$$

$$\mu_{a2} = V\epsilon_2 \quad (31)$$

into equation (29) yield $$\ln\frac{I_1(\mu_{s1}, \mu_{a1})B_2}{kI_1(\mu_{s2}, \mu_{a2})B_1} = (V\epsilon_2 - V\epsilon_1)[p\langle L_1(\mu_{s2}, \mu_{a2})\rangle + \quad (32)$$

$$(1-p)\sqrt{k}\langle L_1(\mu_{s1}, \mu_{a1})\rangle] -$$

$$V\epsilon_1(1-\sqrt{k})\langle L_1(\mu_{s1}, \mu_{a1})\rangle$$

$$= V[(\epsilon_2 - \epsilon_1)[p\langle L_1(\mu_{s2}, \mu_{a2})\rangle +$$

$$(1-p)\sqrt{k}\langle L_1(\mu_{s1}, \mu_{a1})\rangle] -$$

$$\epsilon_1(1-\sqrt{k})\langle L_1(\mu_{s1}, \mu_{a1})\rangle]$$

This yields $$V = \ln\frac{I_1(\mu_{s1}, \mu_{a1})B_2}{kI_1(\mu_{s2}, \mu_{a2})B_1} [(\epsilon_2 - \epsilon_1)[p\langle L_1(\mu_{s2}, \mu_{a2})\rangle + \quad (33)$$

$$(1-p)\sqrt{k}\langle L_1(\mu_{s1}, \mu_{a1})\rangle] - \epsilon_1(1-\sqrt{k})\langle L_1(\mu_{s1}, \mu_{a1})\rangle]^{-1}$$

The present inventors have found that the concentration V of the absorption component can be calculated in accordance with $$V = \ln\frac{I_1(\lambda_1)B_2}{kI_1(\lambda_2)B_1 [(\epsilon_2 - \epsilon_1)\{p\langle L_1(\lambda_2)\rangle + (1-p)\sqrt{k}\langle L_1(\lambda_1)\rangle\} -}$$

$$\epsilon_1(1-\sqrt{k})\langle L_1(\lambda_1)\rangle]^{-1}$$

More specifically, since $\epsilon_1$, $\epsilon_2$, $B_1$, $B_2$, and k (ratio of the transport scattering coefficient) are known, the concentration V of a specific absorption component can be calculated from values obtained by measurement, i.e., the mean flight pathlengths $<L_1(\lambda_1)>$ and $<L_1(\lambda_2)>$, natural logarithms of light intensities $\ln I_1(\lambda_1)$ and $\ln I_1(\lambda_2)$, and the value p that can be empirically defined.

In actual measurement, when p=½ is set for equation (33), and the average values $<L_1(\lambda_1)>$ and $<L_1(\lambda_2)>$ are used for $<L_1(\mu_s,\mu_{ax})>$ to obtain $$<L_1(\mu_s,\mu_{ax})> = \tfrac{1}{2}[<L_1(\lambda_1)> + <L_1(\lambda_2)>] \quad (34)$$

a sufficient measurement accuracy can be obtained.

More generally, when the mean flight pathlengths $<L_1(\lambda_1)>$, $<L_1(\lambda_2)>$, $<L_2(\lambda_1)>$, $<L_2(\lambda_2)>$ and light intensities $I_1(\lambda_1)$, $I_1(\lambda_2)$, $I_2(\lambda_1)$, $I_2(\lambda_2)$ are to be detected for incident light having the wavelength $\lambda_1$ (incident light intensity $B_1$) and wavelength $\lambda_2$ (incident light intensity $B_2$) at photodetection positions $r_1$ and $r_2$, respectively, the difference between equation (35)

$$\ln\frac{I_1(\mu_{sl},\mu_{al})B_2}{kI_1(\mu_{s2},\mu_{a2})B_1} = (V\varepsilon_2 - V\varepsilon_1)[p\langle L_1(\mu_{s2},\mu_{a2})\rangle + \qquad (35)$$

$$(1-p)\sqrt{k}\,\langle L_1(\mu_{sl},\mu_{al})\rangle] -$$

$$V\varepsilon_1\left(1-\sqrt{k}\right)\langle L_1(\mu_{sl},\mu_{al})\rangle$$

$$= V[(\varepsilon_2 - \varepsilon_1)[p\langle L_1(\mu_{s2},\mu_{a2})\rangle +$$

$$(1-p)\sqrt{k}\,\langle L_1(\mu_{sl},\mu_{al})\rangle] -$$

$$\varepsilon_1\left(1-\sqrt{k}\right)\langle L_1(\mu_{sl},\mu_{al})\rangle]$$

and equation (36)

$$\ln\frac{I_2(\mu_{sl},\mu_{al})B_2}{kI_2(\mu_{s2},\mu_{a2})B_1} = (V\varepsilon_2 - V\varepsilon_1)[p\langle L_2(\mu_{s2},\mu_{a2})\rangle + \qquad (36)$$

$$(1-p)\sqrt{k}\,\langle L_2(\mu_{sl},\mu_{al})\rangle] -$$

$$V\varepsilon_1\left(1-\sqrt{k}\right)\langle L_2(\mu_{sl},\mu_{al})\rangle$$

$$= V[(\varepsilon_2 - \varepsilon_1)[p\langle L_2(\mu_{s2},\mu_{a2})\rangle +$$

$$(1-p)\sqrt{k}\,\langle L_2(\mu_{sl},\mu_{al})\rangle] -$$

$$\varepsilon_1\left(1-\sqrt{k}\right)\langle L_2(\mu_{sl},\mu_{al})\rangle]$$

is calculated. The left-hand side is $$\ln\frac{I_2(\mu_{sl},\mu_{al})B_2}{kI_2(\mu_{s2},\mu_{a2})B_1} - \ln\frac{I_1(\mu_{sl},\mu_{al})B_2}{kI_1(\mu_{s2},\mu_{a2})B_1} = \qquad (37)$$

$$\ln\frac{I_2(\mu_{sl},\mu_{al})}{I_2(\mu_{s2},\mu_{a2})} - \ln\frac{I_1(\mu_{sl},\mu_{al})}{I_1(\mu_{s2},\mu_{a2})} = \ln\frac{I_2(\mu_{sl},\mu_{al})I_1(\mu_{s2},\mu_{a2})}{I_2(\mu_{s2},\mu_{a2})I_1(\mu_{sl},\mu_{al})}$$

and the right-hand side is $$V[(\varepsilon_2 - \varepsilon_1)\{p\langle L_2(\mu_{s2},\mu_{a2})\rangle + (1-p)\sqrt{k}\,\langle L_2(\mu_{sl},\mu_{al})\rangle\} - \qquad (38)$$

$$(\varepsilon_2 - \varepsilon_1)\{q\langle L_1(\mu_{s2},\mu_{a2})\rangle + (1-q)\sqrt{k}\,\langle L_1(\mu_{sl},\mu_{al})\rangle\} -$$

$$\varepsilon_1\left(1-\sqrt{k}\right)\langle L_2(\mu_{sl},\mu_{al})\rangle + \varepsilon_1\left(1-\sqrt{k}\right)\langle L_1(\mu_{sl},\mu_{al})\rangle] =$$

$$V[(\varepsilon_2 - \varepsilon_1)\{p\langle L_2(\mu_{s2},\mu_{a2})\rangle + (1-p)\sqrt{k}\,\langle L_2(\mu_{sl},\mu_{al})\rangle\} -$$

$$(\varepsilon_2 - \varepsilon_1)\{q\langle L_1(\mu_{s2},\mu_{a2})\rangle + (1-q)\sqrt{k}\,\langle L_1(\mu_{sl},\mu_{al})\rangle\} -$$

$$\varepsilon_1\left(1-\sqrt{k}\right)\{\langle L_2(\mu_{sl},\mu_{al})\rangle + \langle L_1(\mu_{sl},\mu_{al})\rangle\}]$$

This yields $$V = \ln\frac{I_2(\mu_{sl},\mu_{al})I_1(\mu_{s2},\mu_{a2})}{I_2(\mu_{s2},\mu_{a2})I_1(\mu_{sl},\mu_{al})} \times [(\varepsilon_2 - \varepsilon_1)\{p\langle L_2(\mu_{s2},\mu_{a2})\rangle + \qquad (39)$$

$$(1-p)\sqrt{k}\,\langle L_2(\mu_{sl},\mu_{al})\rangle\} - (\varepsilon_2 - \varepsilon_1)\{q\langle L_1(\mu_{s2},\mu_{a2})\rangle +$$

$$(1-q)\sqrt{k}\,\langle L_1(\mu_{sl},\mu_{al})\rangle\} - \varepsilon_1\left(1-\sqrt{k}\right)\{\langle L_2(\mu_{sl},\mu_{al})\rangle +$$

$$\langle L_1(\mu_{sl},\mu_{al})\rangle\}]^{-1}$$

Hence, the present inventors have found that the concentration V of the absorption component can be calculated in accordance with $$V = \ln\frac{I_2(\lambda_1)I_1(\lambda_2)}{I_2(\lambda_2)I_1(\lambda_1)} \times \left[(\varepsilon_2 - \varepsilon_1)\{p\langle L_2(\lambda_2)\rangle + (1-p)\sqrt{k}\,\langle L_2(\lambda_1)\rangle\} - \right.$$

$$(\varepsilon_2 - \varepsilon_1)\{q\langle L_1(\lambda_2)\rangle + (1-q)\sqrt{k}\,\langle L_1(\lambda_1)\rangle\} -$$

$$\left.\varepsilon_1\left(1-\sqrt{k}\right)\{\langle L_2(\lambda_1)\rangle + \langle L_1(\lambda_1)\rangle\}\right]^{-1}$$

where p is an appropriate value satisfying $0 \leq p \leq 1$, and q is an appropriate value satisfying $0 \leq q \leq 1$.

In this case as well, since $\varepsilon_2$, $\varepsilon_1$, and k (ratio of the transport scattering coefficient) are known, the concentration V of a specific absorption component can be calculated from values obtained by measurement, i.e., the mean flight path-lengths $\langle L_1(\lambda_1)\rangle$, $\langle L_1(\lambda_2)\rangle$, $\langle L_2(\lambda_1)\rangle$, $\langle L_2(\lambda_2)\rangle$, natural logarithms of light intensities $\ln I_1(\lambda_1)$, $\ln I_1(\lambda_2)$, $\ln I_2(\lambda_1)$, $\ln I_2(\lambda_2)$, and the values p and q that can be empirically defined, as described above.

In this case as well, when $p=q=\frac{1}{2}$, equation (39) is rewritten into $$V = 2\ln\frac{I_2(\mu_{sl},\mu_{al})I_1(\mu_{s2},\mu_{a2})}{I_2(\mu_{s2},\mu_{a2})I_1(\mu_{sl},\mu_{al})}[(\varepsilon_2 - \varepsilon_1)\{\langle L_2(\mu_{s2},\mu_{a2})\rangle + \qquad (40)$$

$$\sqrt{k}\,\langle L_2(\mu_{sl},\mu_{al})\rangle\} - (\varepsilon_2 - \varepsilon_1)\{\langle L_1(\mu_{s2},\mu_{a2})\rangle +$$

$$\sqrt{k}\,\langle L_1(\mu_{sl},\mu_{al})\rangle\} - \varepsilon_1\left(1-\sqrt{k}\right)\{\langle L_2(\mu_{sl},\mu_{al})\rangle +$$

$$\langle L_1(\mu_{sl},\mu_{al})\rangle\}]^{-1}$$

Hence, a sufficient measurement accuracy can be obtained.

When the scattering medium contains two types of absorption components, three light components having different wavelengths may be used. More specifically, let $V_1$ and $V_2$ be the concentrations of the two absorption components of the scattering medium. Two simultaneous equations associated with $V_1$ and $V_2$ hold, like equation (33) or (39). When these simultaneous equations are solved, $V_1$ and $V_2$ can be obtained. More generally, when a scattering medium contains m types of absorption components, the concentrations of the m absorption components can be measured using (m+1) light components having of wavelengths.

Figure 4:
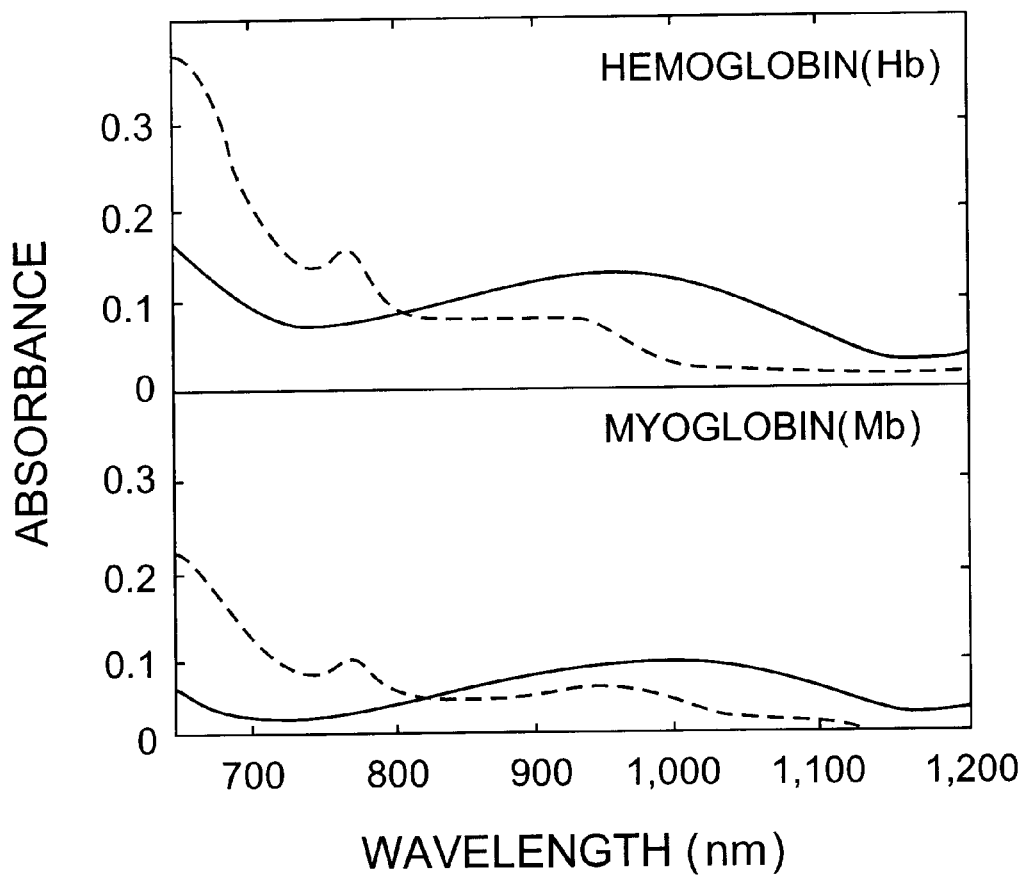
FIG. 4 is a graph showing absorption spectra of various vital substances.

For example, FIG. 4 shows the absorption spectra of oxygenated and deoxygenated hemoglobin and oxygenated and deoxygenated myoglobin. For hemoglobin in a brain, it is important to measure the ratio of an oxygenated component to a deoxygenated component. In this case, measurement based on the above-described principle can be performed using light components with wavelengths having a large absorption coefficient difference for oxygenated and deoxygenated components, i.e., light components having wavelengths from 700 nm to 1.2 $\mu$m.

In the present invention, even when the scattering coefficient of a scattering component changes depending on the wavelength of light, the concentration of the absorption component in the scattering medium can be accurately measured. For this reason, even when the wavelength dependence of the scattering coefficient cannot be neglected as in an actual vital sample, the wavelength to be used is not limited, and measurements of scattering media having various boundary conditions (shapes) are enabled.

The method of measuring the concentrations of specific absorption components in scattering media having various boundary conditions has been described above. In the above embodiment, an impulse response is measured using pulse light. However, the present invention is not limited to this embodiment. For example, modulated light may be used, as will be described below.

When modulated light is to be used, Fourier transform of an impulse response h(t) represents a system function. Considering that the impulse response h(t) is a time causal function, Fourier transform of equation (3) yields a system function $H(\omega)$ given by $$H(\omega) = H(\mu_s, \mu_a, \omega) \quad (41)$$

$$= \int_0^\infty h(t)\exp(-j\omega t)\,dt$$

$$= R(\mu_s, c\mu_a, \omega) + jX(\mu_s, c\mu_a, \omega)$$

$$= A(\mu_s, c\mu_a, \omega)\exp[j\phi(\mu_s, c\mu_a, \omega)]$$

where $R(\mu_s, c\mu_a, \omega)$ and $X(\mu_s, c\mu_a, \omega)$ are the real part and imaginary part, respectively, and $A(\mu_s, c\mu_a, \omega)$ and $\phi(\mu_s, c\mu_a, \omega)$ are the amplitude and phase, respectively. The phase delay is represented by changing the sign of phase.

When equation (3) is substituted into equation (41) and rearranged, the following expressions called Cauchy-Riemann expressions in the complex function theory hold.

$$\frac{\partial R(\mu_s, c\mu_a, \omega)}{\partial c\mu_a} = \frac{\partial X(\mu_s, c\mu_a, \omega)}{\partial \omega} \quad (42.1)$$

$$\frac{\partial R(\mu_s, c\mu_a, \omega)}{\partial \omega} = -\frac{\partial X(\mu_s, c\mu_a, \omega)}{\partial c\mu_a} \quad (42.2)$$

When equations (42.1) and (42.2) hold, it is proved that the following relations hold.

$$\frac{\partial \ln A(\mu_s, c\mu_a, \omega)}{\partial c\mu_a} = \frac{\partial \phi(\mu_s, c\mu_a, \omega)}{\partial \omega} \quad (43.1)$$

$$\frac{\partial \ln A(\mu_s, c\mu_a, \omega)}{\partial \omega} = -\frac{\partial \phi(\mu_s, c\mu_a, \omega)}{\partial c\mu_a} \quad (43.2)$$

Hence, to calculate the absorption coefficient $\mu_a$, any one of equations (42.1), (42.2), (43.1), and (43.2) can be used. More specifically, equations obtained by integrating these equations by $\mu_a$, i.e., the following equations obtained from the above equations are preferably used.

$$R(\mu_s, c\mu_a, \omega) = c\int_0^{\mu_a}\frac{\partial X(\mu_s, c\mu_a, \omega)}{\partial \omega}d\mu_a + R(\mu_s, 0, \omega) \quad (44.1)$$

$$X(\mu_s, c\mu_a, \omega) = -c\int_0^{\mu_a}\frac{\partial R(\mu_s, c\mu_a, \omega)}{\partial \omega}d\mu_a + X(\mu_s, 0, \omega) \quad (44.2)$$

$$\ln A(\mu_s, c\mu_a, \omega) = c\int_0^{\mu_a}\frac{\partial \phi(\mu_s, c\mu_a, \omega)}{\partial \omega}d\mu_a + \ln A(\mu_s, 0, \omega) \quad (44.3)$$

$$\phi(\mu_s, c\mu_a, \omega) = -c\int_0^{\mu_a}\frac{\partial \ln A(\mu_s, c\mu_a, \omega)}{\partial \omega}d\mu_a + \phi(\mu_s, 0, \omega) \quad (44.4)$$

The second term of the right-hand side of each of equations (44.1) to (44.4) is an integration constant representing a value for $\mu_a=0$. When analysis is performed using equations (44.1) to (44.4) in the above-described way, an equation like equation (33) or (39) related to the concentration of an absorption component in a scattering medium can be derived. More specifically, equation (44.3) corresponds to the above-described equation (12). Hence, even when modulated light is used, the above-described analysis can be performed by replacing the integration intensity I with the amplitude A and the mean optical pathlength <L> with the phase $\phi$. When intensity-modulated light is used, $B_1$ and $B_2$ in the above equation are the amplitudes of the modulation frequency components of the intensity-modulated light.

In the above embodiment, as the detection light intensity I, a value obtained by integrating the time-resolved waveform within the range from time 0 to infinity (as a practical method for measurement, the range is until the observed light waveform sufficiently attenuates) is employed (e.g., equation (7)). However, the present invention is not limited to this. For example, a period from arbitrary time $t_1$ to $t_2$ may be set, and the light waveform may be integrated within this range to perform analysis as described above. In this case, since the optical pathlength of photons transmitted through the interior of the scattering medium as a target measurement object can be limited, the measurement region can be limited.

The embodiments of the present invention will be described below with reference to the accompanying drawings. The same reference numerals denote the same elements throughout the drawings, and a repetitive description thereof will be omitted.

First Embodiment

Figure 5:
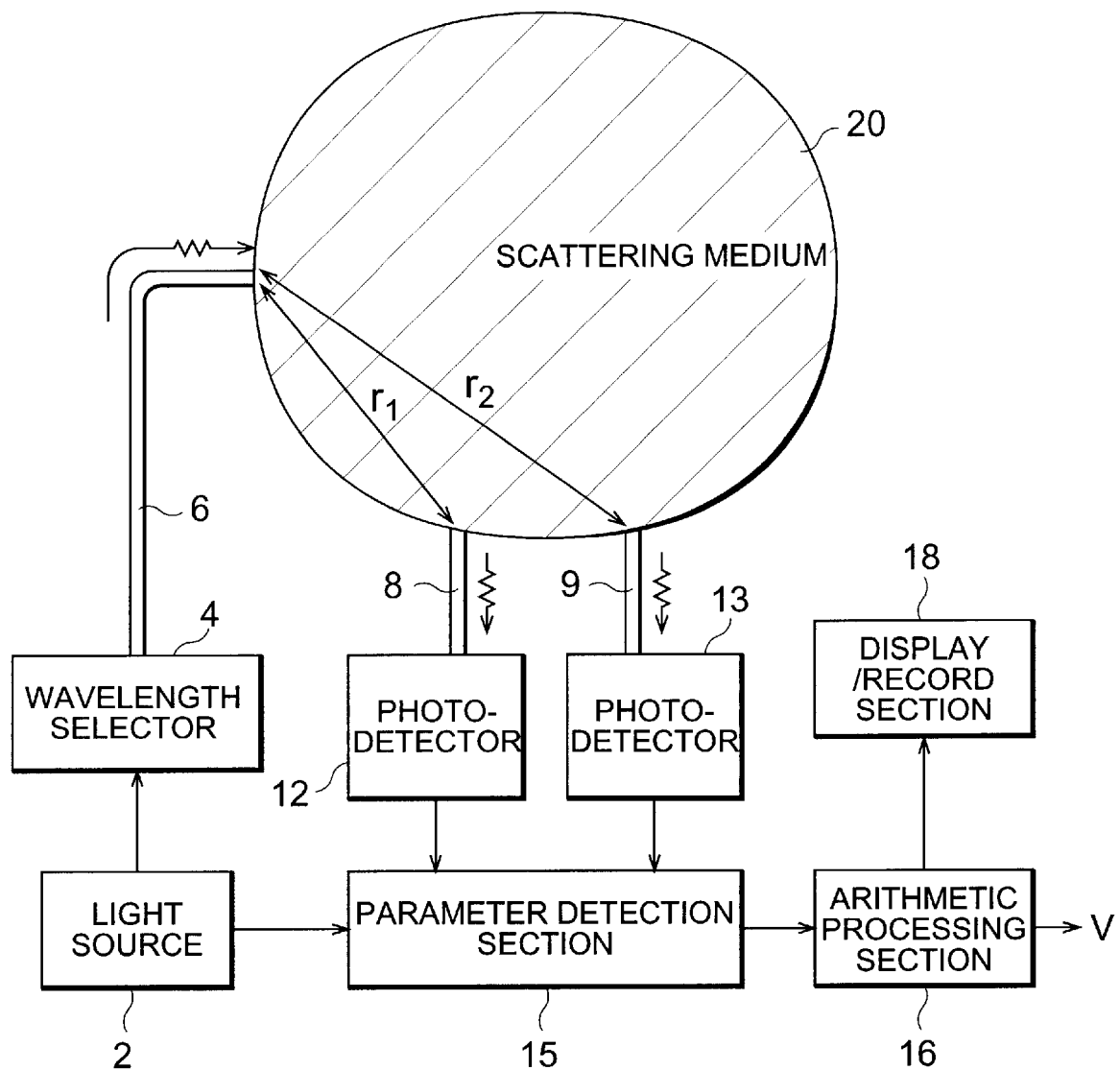
FIG. 5 is a schematic view showing the arrangement of an apparatus according to the first embodiment.

FIG. 5 shows the first embodiment of a method and an apparatus for measuring the concentration of an absorption component in a scattering medium 20 according to the present invention. In this embodiment, since eight parameter values can be obtained in correspondence with two light components having different wavelengths ($\lambda_1$ and $\lambda_2$) and two photodetection distances ($r_1$ and $r_2$), the concentration of the absorption component can be measured using the above-described equation (39).

A light source 2 generates pulse light (pulse light rays) having different wavelengths $\lambda_1$ and $\lambda_2$ using a laser diode. The time width of the pulse light can be freely selected within, normally, a range of 10 ps to 100 ns provided that it is so short that the mean flight pathlength can be obtained from a photodetection signal. Further, the wavelengths of the light need to be suitably selected corresponding to the object to be measured. Generally, for a living body, light having a wavelength of 700 nm or more is often used from the viewpoint of absorption by hemoglobin or the like. For the light source, not only the laser diode but also a light-emitting diode, HeNe laser, titanium sapphire laser, or the like may be used.

The wavelength of pulse light from the light source 2 is selected by a wavelength selector 4. The pulse light is incident onto the surface of the scattering medium 20 as a target measurement object through a light guide 6. In this case, two pulse light components having different wavelengths may be made simultaneously incident. In this case, the wavelength selector 4 is omitted.

The space between the light guide 6 and the scattering medium 20 is very small in the embodiment shown in FIG. 5. Actually, the space may be increased and filled with a liquid or gel object (to be referred to as an interface material hereinafter) having a refractive index and scattering coefficient almost equal to those of the scattering medium 20. That is, since light diffuses and propagates through this interface material and becomes incident on the target measurement object, no problem is posed. If surface reflection of the scattering medium poses a problem, the influence of surface reflection can be reduced by appropriately selecting an interface material.

The light that has diffused and propagated inside the scattering medium is received by light guides 8 and 9 located at positions separated from the light incident position by the distances $r_1$ and $r_2$. An interface material may also be used at these positions due to the same reason as described above.

A first photodetector 12 and second photodetector 13 convert the optical signals into electrical signals, amplify the signals as needed, and output photodetection signals. For the photodetectors 12 and 13, not only a photomultiplier but also a photoelectric tube, photodiode, avalanche photodiode, or PIN photodiode can be used. Any photodetector can be selected as far as it has spectral sensitivity characteristics for detecting light having a predetermined wavelength and necessary time response speed. If the optical signal is weak, a photodetector with a high gain is used. A time correlated photon counting method of counting photons may be used. A structure other than the light-receiving surface of the photodetector preferably absorbs or shields light. When two pulse light components having different wavelengths are to be made simultaneously incident on the scattering medium, as described above, appropriate wavelength selection filters (not shown) are preferably inserted between the photodetector 12 and the scattering medium 20 and between the photodetector 13 and the scattering medium 20.

A parameter detection section 15 detects the light intensity and mean flight pathlength from each photodetection signal. The light intensity is the time-integrated value of a photodetection signal, and therefore, can easily be obtained by integrating the photodetection signal. The mean flight pathlength is the weighted average of the time waveform of a photodetection signal with respect to the incidence of pulse light having a sufficiently small time width, and therefore, can easily be obtained by executing the above-described equation (10) or equivalent calculation on the basis of the time waveform of the photodetection signal. In this case, the parameter detection section uses a signal synchronized with the optical pulse generation by the light source 2, as needed.

An arithmetic processing section 16 calculates a concentration V of the absorption component on the basis of the above-described equation (39) using the eight parameter values obtained by the parameter detection section 15, i.e., the light intensities $I_1(\lambda_1)$ and $I_1(\lambda_2)$ and mean flight pathlengths $<L_1(\lambda_1)>$ and $<L_1(\lambda_2)>$ at the position $r_1$ and the light intensities $I_2(\lambda_1)$ and $I_2(\lambda_2)$ and mean flight pathlengths $<L_2(\lambda_1)>$ and $<L_2(\lambda_2)>$ at the position $r_2$ for incidence of pulse light having wavelengths $\lambda_1$ and $\lambda_2$. At this time, constants p and q which can be empirically defined are used. In actual measurement, a sufficient accuracy is obtained by setting p=q=½. These calculations are executed at a high speed by a microcomputer incorporated in the arithmetic processing section.

If the incident light intensities of the pulse light components having the wavelengths $\lambda_1$ and $\lambda_2$ are equal or can be controlled to be equal, the second photodetector 13 can be omitted. In this case, four parameters, i.e., the light intensities $I_1(\lambda_1)$ and $I_1(\lambda_2)$ and mean flight pathlengths $<L_1(\lambda_1)>$ and $<L_1(\lambda_2)>$ at the position $r_1$ for incidence of pulse light having the wavelengths $\lambda_1$ and $\lambda_2$ are obtained by the parameter detection section 15. Hence, the arithmetic processing section 16 calculates the concentration V of the absorption component on the basis of the above-described equation (33) using these parameter values. At this time, the constant p that can be empirically defined is used. In actual measurement, a sufficient accuracy can be obtained by setting p=½. These calculations are executed at a high speed by a microcomputer incorporated in the arithmetic processing section.

The method of making light incident from one position and detecting it at two other positions has been described above. In fact, light beams having different wavelengths may be made incident from two positions and parallelly or time-divisionally detected at other positions.

As described above, in this embodiment, a method of making light containing light components having different wavelengths incident or a method of time-divisionally making light components having different wavelengths incident is used. For the former method, a method of making the light components having different wavelengths incident as coaxial beams and selecting a wavelength by a wavelength selection filter arranged immediately beforefthle light incident position, a method of making the light components directly incident on the scattering medium and selecting a wavelength by a wavelength selection filter arranged immediately before the photodetector, or a method of splitting each detected light component into two divisions, selecting wavelengths, and parallelly detecting the light components by a total of four photodetectors can be used. For the latter method, a light ray switching device using a mirror on the light source side, a wavelength switching device using a filter, or a light switching device using an optical switch can be used.

Figure 6A:
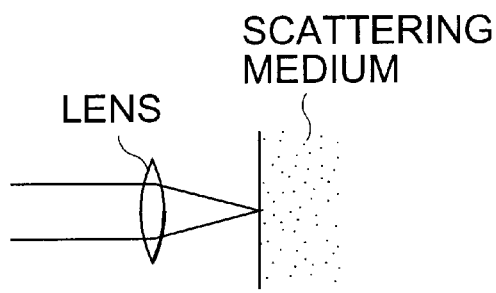
FIGS. 6A to 6D are schematic views showing methods of making light incident to a scattering medium.
Figure 6B:
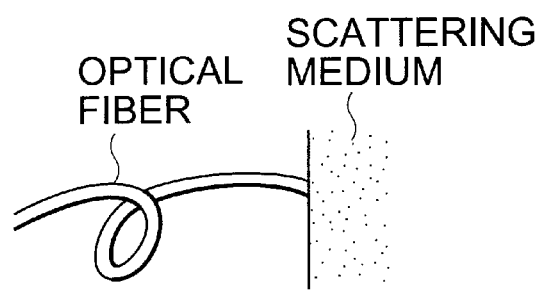
Figure 6C:
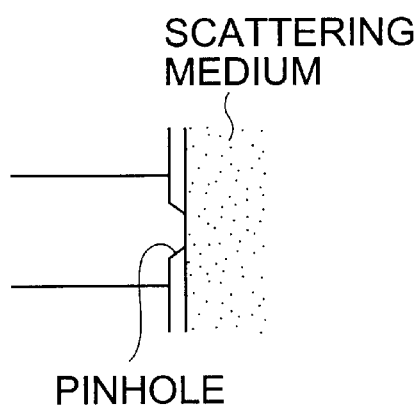
Figure 6D:
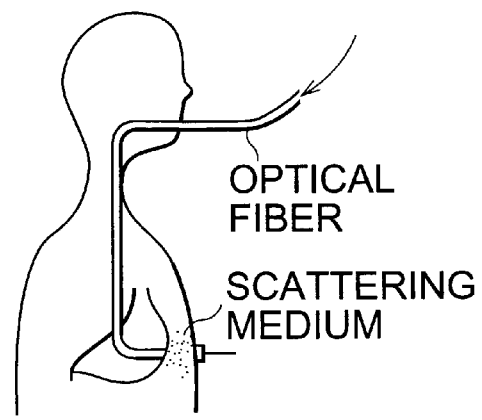

As a means for making light incident on the scattering medium, a method using a condenser lens (FIG. 6A), a method using an optical fiber (FIG. 6B), a method using a pinhole (FIG. 6C), a method of making light incident in the body cavity (scattering medium) using, e.g., a gastroscope (FIG. 6D) may be used instead of the method using the light guide shown in FIG. 5. Alternatively, a thick light beam may be made incident on the scattering medium. This can be regarded that a plurality of spot-like light sources are arranged.

Figure 7A:
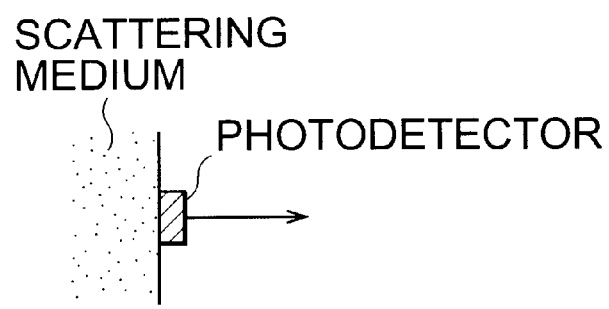
FIGS. 7A to 7C are schematic views showing methods of receiving light.
Figure 7B:
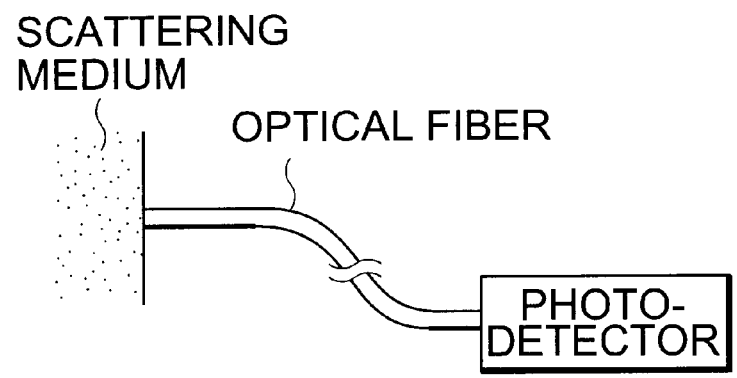

As a means for detecting the light that has diffused and propagated inside the scattering medium, not only the method using the light guide shown in FIG. 5 but also a method (f directly detecting the light (FIG. 7A), a method using an optical fiber (FIG. 7B), or a method using a lens (FIG. 7C) can be used.

In the first embodiment, when three light components having different wavelengths are used, the concentration of each of two absorption components contained in a scattering medium, or the concentration of one of a number of absorption components contained in a scattering medium and the total concentration of the remaining absorption components can be measured. For example, oxygenated hemoglobin and deoxygenated hemoglobin exhibit different absorption coefficients depending on the wavelength, as shown in FIG. 4. Hence, when three light components having different wavelengths appropriately selected are used, the concentration and, additionally, the oxygen saturation of each of the absorption components can be measured. Generally, when (m+1) light components having different wavelengths are used, the concentrations of m absorption components can be measured. When light components larger in number than (m+1) are used, the measurement accuracy can be improved.

When measurement is executed at different times, a change in time of the concentration of the absorption component can be measured. When the concentrations of the absorption components at various portions of the scattering medium are measured by scanning it while synchronizing the light incident positions on the scattering medium with the light detection positions, the spatial distribution of the concentrations can be measured. The arithmetic processing section 16 has a function of storing concentration information obtained in the above way, and a display/record means 18 displays or records the concentration information.

These calculations can be executed at a high speed by a computer apparatus having a memory and display.

Second Embodiment

Figure 8:
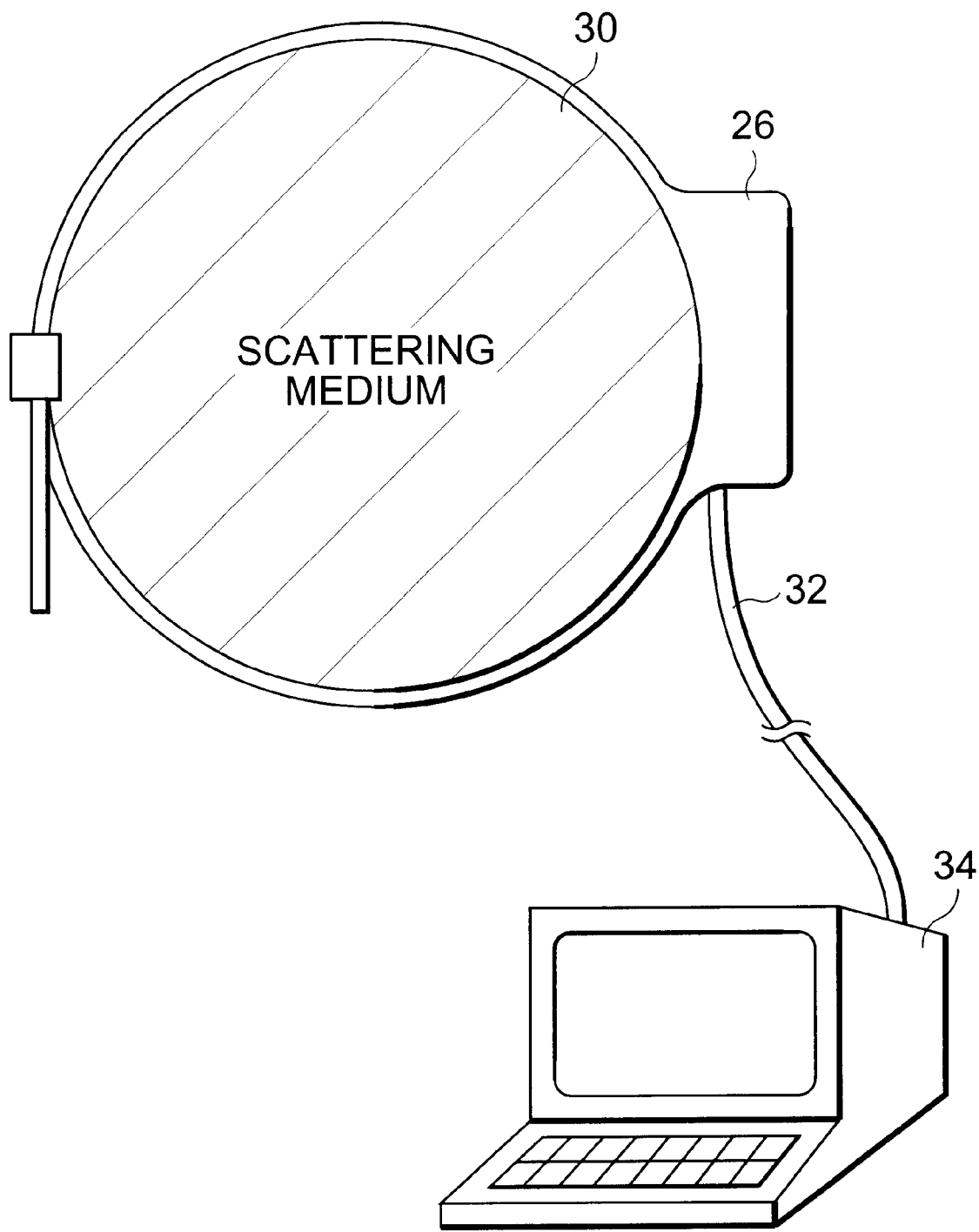
FIG. 8 is a schematic view showing the arrangement of an apparatus according to the second embodiment.

FIG. 8 shows the second embodiment of the present invention, i.e., a method and apparatus for measuring or monitoring the concentration of oxygenated hemoglobin or oxygen saturation of hemoglobin (ratio of the concentration of oxygenated hemoglobin to the concentration of entire hemoglobin) in a scattering medium 30 such as a human head portion. In this embodiment, 12 parameter values obtained using three light components having different wavelengths ($\lambda_1$, $\lambda_2$, $\lambda_3$) and two photodetection distances ($r_1$ and $r_2$) are substituted into three simultaneous equations based on the above-described equation (20), thereby measuring the concentration of oxygenated hemoglobin and oxygen saturation of hemoglobin.

Figure 9:
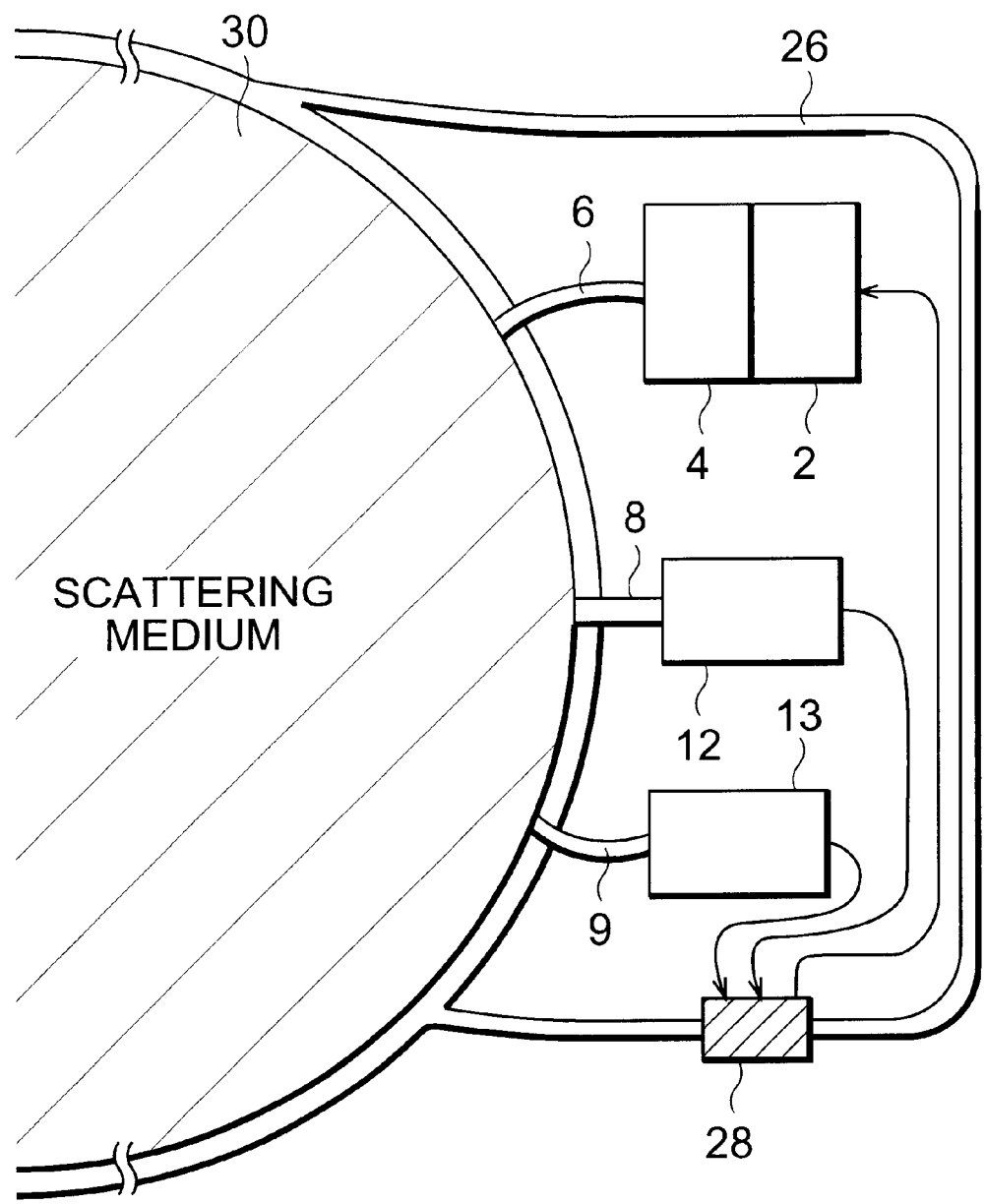
FIG. 9 is a schematic view showing the arrangement of a light incidence/detection section of the apparatus according to the second embodiment.

A vessel 26 with a fit belt is wound on the head portion 30 like a headband. The apparatus of this embodiment uses three light components having predetermined wavelengths $\lambda_1$, $\lambda_2$, and $\lambda_3$, and its operation is almost the same as that of the apparatus of the first embodiment. FIG. 9 shows part of the arrangement of the apparatus shown in FIG. 8, i.e., the detailed internal structure of the vessel 26.

Referring to FIG. 9, a wavelength of pulse light components having the predetermined wavelengths $\lambda_1$, $\lambda_2$, and $\lambda_3$ emitted from a light source 2 is selected by a wavelength selector 4, and the selected light component is incident on the head portion 30 through a light guide 6. The three wavelengths are appropriately selected with reference to the absorption spectrum of hemoglobin shown in FIG. 4.

The light that has diffused and propagated inside the head portion is received by light guides 8 and 9 located at positions separated from the light incident position by the distances $r_1$ and $r_2$ and converted into electrical signals, and amplified as needed, by the first photodetector 12 and second photodetector 13. Resultant signals are signals corresponding to the three wavelengths and two photodetection distances. The power supply and various signals are connected to an external device 34 by a signal cable 32 through a connector 28 attached to the vessel 26. A parameter detection section (not shown) in the external device 34 obtains light intensities and mean flight pathlengths corresponding to the three wavelengths and two photodetection distances, i.e., 12 parameters.

At this time, two simultaneous equations like the above-described equation (39) hold for signals obtained in relation to the wavelengths $\lambda_1$ and $\lambda_2$ and those obtained in ralation to the wavelengths $\lambda_1$ and $\lambda_3$. As in the first embodiment, a concentration $V_1$ of oxygenated hemoglobin, a concentration $V_2$ of deoxygepnated hemoglobin, and oxygen saturation $V_1/(V_1+V_2)$ of hemoglobin can be calculated by an arithmetic processing section (not shown), and output or displayed as needed. These calculations are executed at a high speed by a microcomputer incorporated in the arithmetic processing section. A signal may be converted into a radio wave or optical signal in the vessel 26 and transmitted to the external device 34 without using a signal cable.

In the above case, the same light source, light incident section, and photodetection means as described in the first embodiment can be used. At a human head portion, surface reflection or a gap between the light guide and the head portion may pose a problem. In such a case, the above-mentioned interface material can be used. The light guide shown in FIG. 9 is omitted, and an interface material having almost the same scattering absorption coefficients as those of the target measurement object is inserted between the head portion and the wavelength selector 4 and between the head portion and the photodetectors 12 and 13.

This apparatus can be used not only for measurement in a brain but also measurement or monitoring of e.g., the oxygenated hemoglobin concentration in leg muscle of a runner during a marathon.

Third Embodiment

Figure 10:
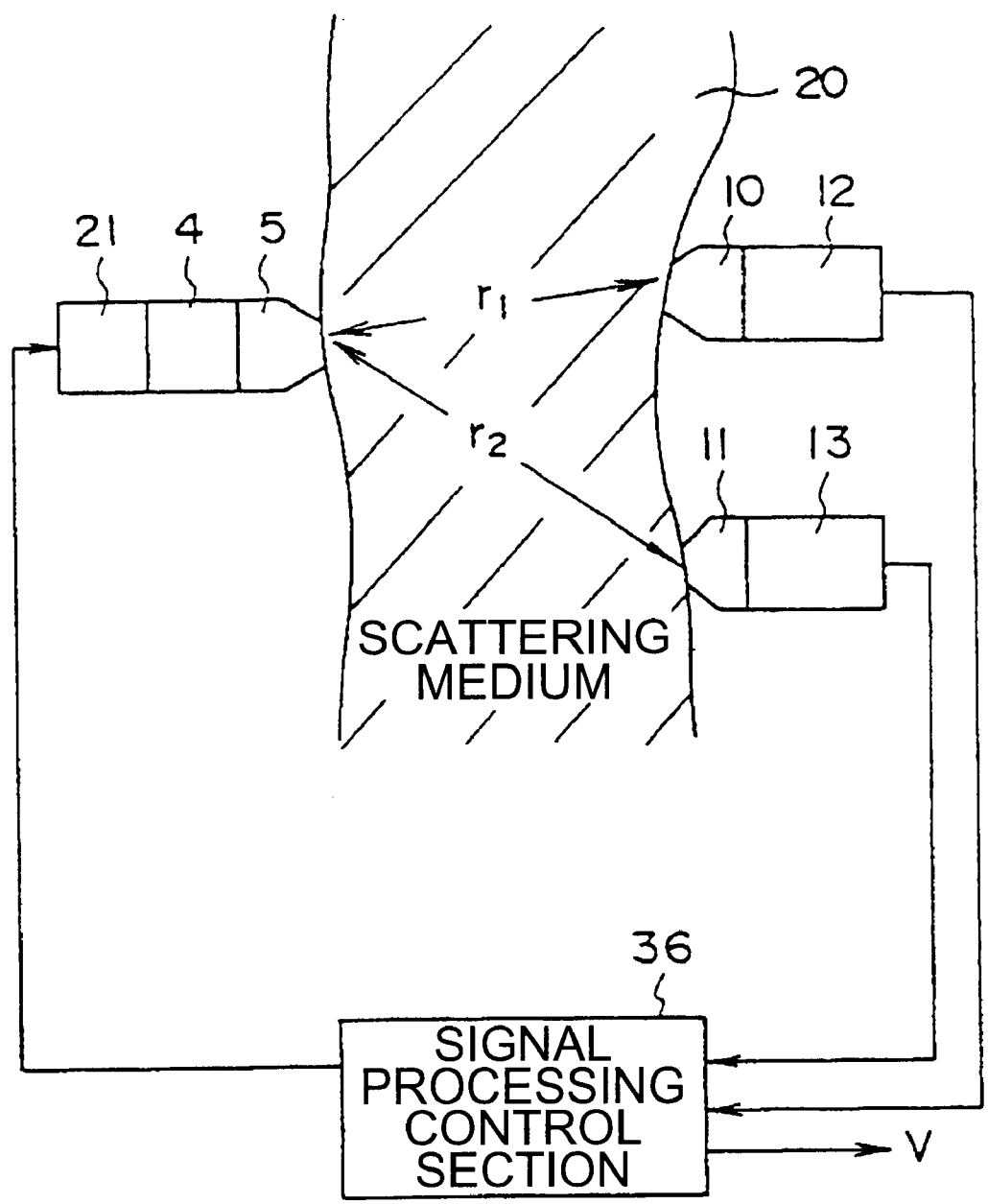
FIG. 10 is a schematic view showing the arrangement of an apparatus according to the third embodiment.

FIG. 10 shows the third embodiment, i.e., a method and apparatus for measuring the concentration of an absorption component in a scattering medium 20 using a sine-wave-modulated light. In this embodiment, a transmission-type constitution is used for measurement. Two modulated light components having different wavelengths ($\lambda_1$ and $\lambda_2$) are made incident, light is detected at two positions corresponding to photodetection distances ($r_1$ and $r_2$), and resultant parameter values are.substituted into the above-described equation (39) to measure the concentration of the absorption component.

Sine-wave-modulated light components having the wavelength (optical wavelength) $\lambda_1$ and $\lambda_2$ and a predetermined angular frequency (modulation angular frequency) $\omega$, which is generated by a modulated light source 21, are guided to a light incident section 5 through a. wavelength selector 4 and made incident on the scattering medium 20. The light incident section uses-the method shown in FIG. 6A, i.e., a lens. However, any other method can be used.

Figure 11A:
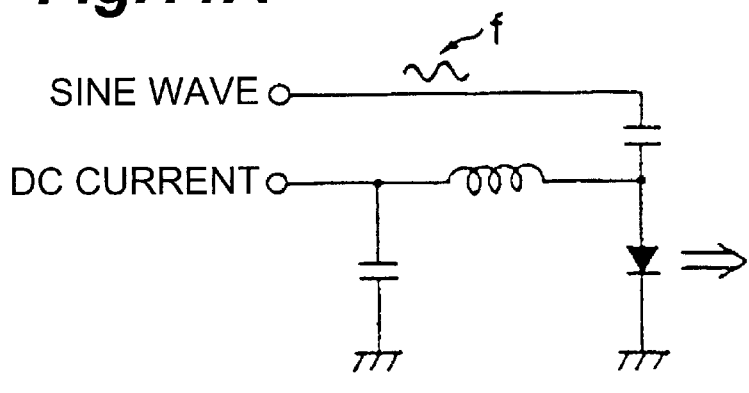
FIGS. 11A, 11C, and 11E are schematic views showing methods of generating modulated light.
Figure 11B:
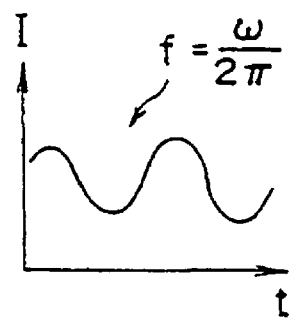
FIGS. 11B, 11D, and 11F are schematic views showing modulated light obtained by the methods.
Figure 11C:
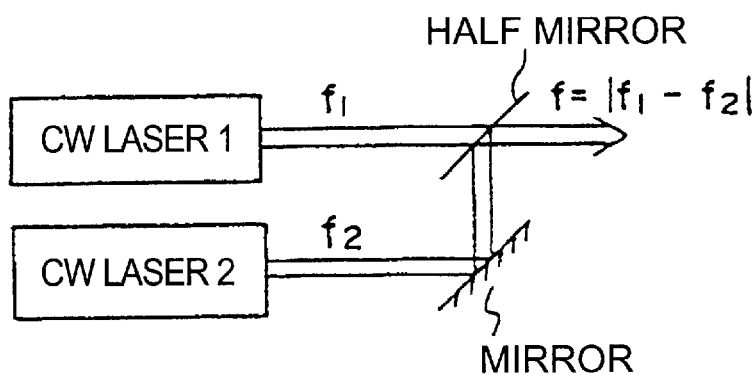
Figure 11D:
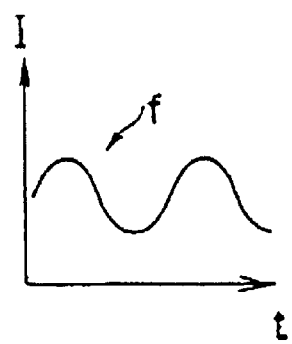
Figure 11E:
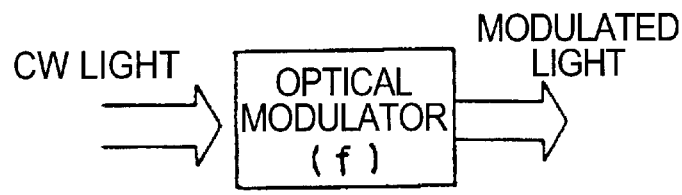
Figure 11F:
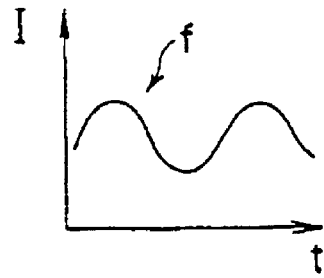

Sine-wave-modulated light having a predetermined angular frequency is generated by current modulation of a laser diode, as shown in FIGS. 11A and 11B. Sine-wave-modulated light can also be generated using the beats of two CW lasers, as shown in FIGS. 11C and 11D, or an optical modulator as shown in FIGS. 11E and 11F.

Figure 7C:
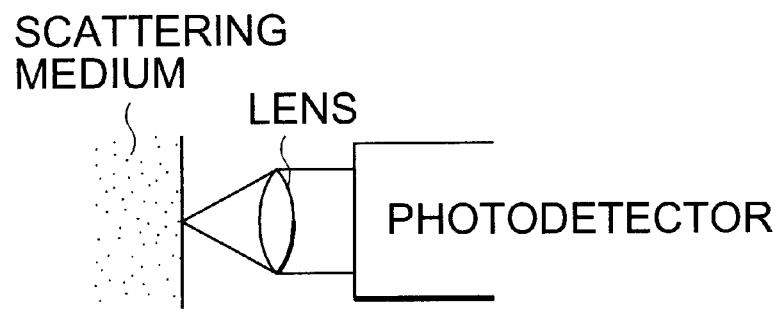

The sine-wave-modulated light incident on the scattering medium 20 via the light incident section 5 diffuses and propagates inside the scattering medium, and a portion thereof is incident to a first light-receiving section 10 and second light-receiving section 11. As the light-receiving section, the method shown in FIG. 7C is used. The light to the light-receiving sections 10 and 11 are converted into electrical signals by photodetectors 12 and 13, respectively. The signals are amplified as needed. In this case, the light incident point and the light-receiving point are separated by the distances $r_1$ and $r_2$.

A signal processing control section 36 performs control of the light source and arithmetic processing of the photodetection signal, outputs a concentration V of the absorption component in the scattering medium 20, and displays and records it as needed.

Figure 12:
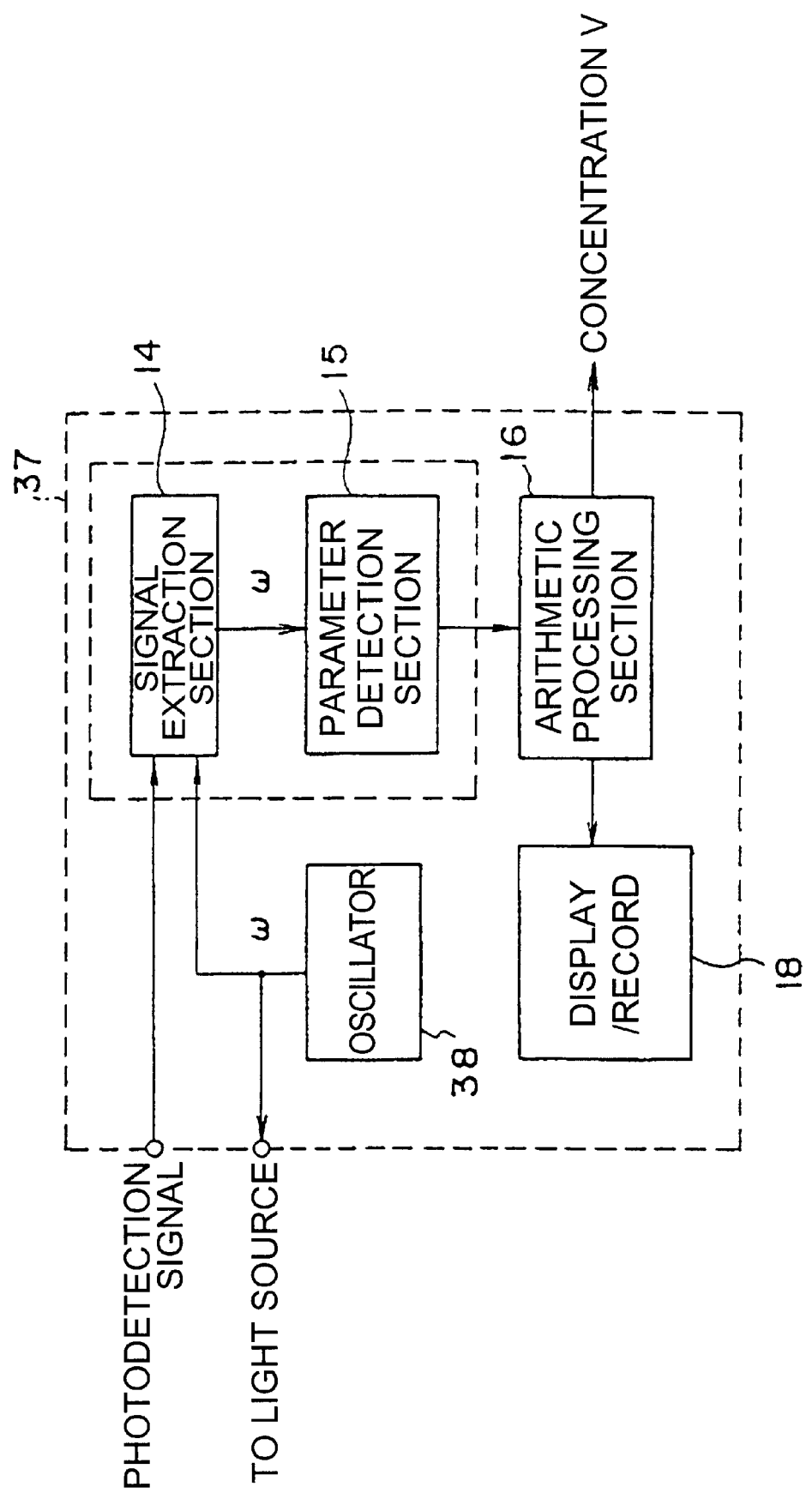
FIG. 12 is a schematic view showing the arrangement of a photodetection signal calculation section.

FIG. 12 shows the detailed arrangement of a section for executing arithmetic processing of the photodetection signal. Photodetection signals from the photodetectors 12 and 13 are guided to a signal extraction section 14, and only a signal whose angular frequency component has a predetermined value $\omega$ is extracted from each photodetection signal. This signal having the predetermined angular frequency $\omega$ is a photon density wave having the predetermined angular frequency $\omega$, which has diffused and propagated inside the scattering medium 20. Subsequently, a parameter detection section 15 detects an amplitude M and phase delay $\phi$ of the signal having the predetermined angular frequency $\omega$.

The behavior of the modulated light in the scattering medium is represented by Fourier transform of equations (3) to (10). At this time, the amplitude ratio of the signals having the predetermined angular frequency $\omega$, which are detected at the detection distance $r_1$ for the predetermined wavelengths $\lambda_1$ and $\lambda_2$, i.e., $M_1(\lambda_1)/M_1(\lambda_2)$ is given by $$\frac{M_1(\lambda_1)}{M_1(\lambda_2)} = \frac{I_1(\lambda_1)}{I_1(\lambda_2)}$$

where $I(\lambda_1)$ and $I(\lambda_2)$ are light intensities used for the above-described equation (39). Hence, the light intensity ratio in equation (33) or (39) equals the amplitude ratio.

When the angular frequency $\omega$ is much lower than the product of the light velocity in the medium and the absorption coefficient, i.e., $\omega \ll c\mu_a$, the phase delay $\phi$ is proportional to the above-described mean flight pathlength $<L(\mu_s, \mu_a)>$.

For example, the phase delay $\phi$ in transmission-type measurement shown in FIG. 10 is given by $$\phi(\mu_s, r, \omega) = \omega c^{-} <L(\mu_s, \mu_a)>$$

Hence, the mean flight pathlength $<L(\mu_s, \mu_a)>$ can be easily obtained from the known values $\omega$ and c and the measurement value $\phi$. Such relationship also holds even for semi-infinite space reflection-type measurement. If the angular frequency is high, not $$<L(\mu_s, \mu_a)> = c\phi(\mu_s, r, \omega)/\omega$$

but $$<L(\mu_s, \mu_a)> = cd\phi(\mu_s, r, \omega)/d\omega$$

is used. That is, a change in phase is measured while slightly changing the modulation angular frequency.

Thus, measurement value parameters required in the calculation of the concentration V of the absorption component using the above-described equation (33) or (39), i.e., the light intensity ratios $I_1(\lambda_1)/I_1(\lambda_2)$ and $I_2(\lambda_1)/I_2(\lambda_2)$ and mean flight pathlengths $<L_1(\lambda_1)>$ and $<L_1(\lambda_2)>$, and $<L_2(\lambda_1)>$ and $<L_2(\lambda_2)>$ at the photodetection distances $r_1$ and $r_2$ for incident light components having the wavelengths $\lambda_1$ and $\lambda_2$ are obtained. As in the first embodiment, constants p and q which can be empirically defined are used. In actual measurement, a sufficient accuracy is obtained by setting p=q=½.

An arithmetic processing section 16 executes the calculation represented by the above-described equation (33) or (39) using the obtained parameters and outputs the concentration V of the absorption component. This concentration value is displayed and recorded as needed. These calculations are normally executed at a high speed by a computer apparatus having a memory and display.

Commercially available lock-in amplifiers may be used for the signal extraction section 14 and parameter detection section 15. A lock-in amplifier can extract a signal having the predetermined frequency component (modulation frequency) $\omega$ from a photodetection signal and detect the amplitude M and phase delay $\phi$ of the signal. At this time, the signal having the angular frequency $\omega$, which is in synchronism with the modulated light, is used as a reference signal. A commercially available lock-in amplifier normally has a modulation frequency measurement range up to 200 kHz. For example, a modulation frequency of 100 MHz cannot be directly measured by a lock-in amplifier. For such measurement, another local transmitter of a frequency slightly different from the modulation frequency of the light source is used, and frequency conversion is performed by the heterodyne method. For example, when the modulation frequency of the light source is 100 KHz, the frequency of the local transmitter is set at 100 MHz+1 kHz, and both signals are input to a mixer, thereby obtaining a 1-kHz output signal. This signal of 1 kHz holds the amplitude and phase information of the input 100-MHz signal and therefore can be measured by a lock-in amplifier.

In the above case, a DC component $m_{dc}$ of each of the photodetection signals from the photodetectors 12 and 13 has a value when $\omega=0$. This value corresponds to the light intensity I in equations (33) and (39). The DC component $m_{dc}$ can be easily detected using a low-pass filter. In the third embodiment, in place of the amplitude of the signal having the predetermined angular frequency $\omega$, the DC component $m_{dc}$ detected at the detection distance $r_1$ or $r_2$ for a predetermined wavelength may be used.

When the above measurement is executed at different times, a change in time of the concentration of the absorption component can be measured. In the above arrangement, when the light incident position and light detection position are synchronously scanned relative to the scattering medium 20 (not shown), the spatial distribution of the concentration of the absorption component can be measured. To do this, a photodetection system having a plurality of channels may be used.

In addition, when three light components having different wavelength are used, the concentration of each of two absorption components contained in a scattering medium, or the concentration of one of a number of absorption components contained in a scattering medium and the total concentration of the remaining absorption components can be measured. More generally, when (m+1) light components having different wavelengths are used, the concentration of each of m absorption components can be measured. When light components larger in number than (m+1) are used, the measurement accuracy can be improved.

These calculations are normally executed at a high speed by a computer apparatus having a memory and display.

Fourth Embodiment

In this embodiment, modulated light having an arbitrary waveform and a predetermined repetitive frequency (modulation frequency) is used in place of the sine-wave-modulated light in the third embodiment, which has the wavelength $\lambda_1$ or $\lambda_2$ and a predetermined frequency andis generated by the light source. More specifically, although sine-wave-modulated light having a predetermined angular frequency is used in the third embodiment, the method of the third embodiment can be directly applied to a specific frequency component in modulated light independently of the waveform as long as the modulated light contains a predetermined frequency component. For example, since repetitive pulse light contains the same frequency as the repetitive frequency and a frequency component of an integer multiple thereof, the method of the third embodiment can be directly applied to any one of the frequency components. Performance required for modulated light having a predetermined repetitive frequency includes a stable repetitive frequency and stable light intensity.

As has been described above, according to the method and apparatus for measuring the concentration of an absorption component in a scattering medium of the present invention, even when scattering characteristics depend on the wavelength, a relative value or an absolute value of concentration of a specific absorption component in a scattering medium having various boundary conditions (shapes) can be measured without any limitation on the wavelength to be used and any influence-of the wavelength dependence of such scattering characteristics. Hence, the measurement accuracy can be greatly improved. According to the present invention, a change in time and spatial distribution of the relative value or the absolute value of concentration of the specific absorption component can also be accurately measured without any influence of the wavelength dependence of scattering characteristics.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A concentration measuring method for an absorption component in a scattering medium, comprising:
   a light generation step of generating at least two light rays having predetermined wavelengths, the light rays having different transport scattering coefficients for a scattering medium as an object to be measured, and a known ratio of the transport scattering coefficients;
   a light incidence step of making the light rays incident from a light incident position into the scattering medium;
   a photodetection step of detecting the light ray which has propagated inside the scattering medium at at least one photodetection position different from the light incident position to acquire at least one photodetection signal;
   a parameter detection step of detecting, on the basis of the photodetection signal, a light intensity and a mean flight pathlength at the light detection position for each of the at least two light rays having predetermined wavelengths; and
   an arithmetic processing step of calculating a concentration of an absorption component on the basis of a predetermined relationship between the ratio of the transport scattering coefficients, the light intensity, the mean flight pathlength, and a difference between absorption coefficients per unit concentration of the absorption component for the at least two light rays having predetermined wavelengths, said predetermined relationship being a relationship derived on the basis of a fact that a value obtained by partially differentiating a natural logarithm of the detected light intensity by the absorption coefficient equals the mean flight pathlength without neglecting a difference in mean flight pathlength due to the difference in scattering coefficients.

2. A method according to claim 1, wherein each of the at least two light rays having predetermined wavelengths is a pulse light ray.

3. A method according to claim 1, wherein each of the at least two light rays having predetermined wavelengths is a sine-wave-modulated light ray having a predetermined modulation frequency component,
   the light intensity is calculated from an amplitude of a signal having the predetermined modulation frequency component, which is contained in the photodetectionrsignal, and
   the mean flight pathlength is calculated from a phase delay of the signal having the predetermined modulation frequency component.

4. A method according to claim 1, wherein each of the at least two light rays having predetermined wavelengths is a sine-wave-modulated light ray having a predetermined modulation frequency component,
   the light intensity is calculated from a DC component of the photodetection signal, and
   the mean flight pathlength is calculated from a phase delay of a signal having the predetermined modulation frequency component, which is contained in the photodetection signal.

5. A method according to claim 1, wherein each of the at least two light rays having predetermined wavelengths is a modulated light ray having a predetermined repetitive frequency component,
   the light intensity is calculated from an amplitude of a signal having the predetermined repetitive modulation frequency component or a frequency component of an integer multiple thereof, which is contained in the photodetection signal, and
   the mean flight pathlength is calculated from a phase delay of the signal having the predetermined repetitive modulation frequency component or the frequency component of an integer multiple thereof.

6. A method according to claim 1, wherein each of the at least two light rays having predetermined wavelengths is a modulated light ray having a predetermined repetitive frequency component,
   the light intensity is calculated from a DC component of the photodetection signal, and
   the mean flight pathlength is calculated from a phase delay of a signal having the predetermined repetitive modulation frequency component or a frequency component of an integer multiple thereof, which is contained in the photodetection signal.

7. A method according to claim 1, wherein the arithmetic processing step comprises calculating the concentration of the absorption component in the scattering medium on the basis of a relationship represented by $$V = \ln \frac{I_1(\lambda_1)B_2}{kI_1(\lambda_2)B_1 \left[(\varepsilon_2 - \varepsilon_1)\{p\langle L_1(\lambda_2)\rangle + (1-p)\sqrt{k}\langle L_1(\lambda_1)\rangle\} - \varepsilon_1(1-\sqrt{k})\langle L_1(\lambda_1)\rangle\right]^{-1}}$$

where
   V is the concentration of the absorption component,
   $\varepsilon_1$ is an absorption coefficient per unit concentration of the absorption component for light having a wavelength $\lambda_1$,
   $\varepsilon_2$ is an absorption coefficient per unit concentration of the absorption component for light having a wavelength $\lambda_2$,
   $\langle L_1(\lambda_1)\rangle$ is a mean flight pathlength for the light having the wavelength $\lambda_1$,
   $\langle L_1(\lambda_2)\rangle$ is a mean flight pathlength for the light having the wavelength $\lambda_2$,
   $I_1(\lambda_1)$ is a detected light intensity for light having an incident light intensity $B_1$ and the wavelength $\lambda_1$,
   $I_1(\lambda_2)$ is a detected light intensity for light having an incident light intensity $B_2$ and the wavelength $\lambda_2$,
   k is a ratio ($\mu_{s2}'/\mu_{s1}'$) of a transport scattering coefficient $\mu_{s2}'$ for the light having the wavelength $\lambda_2$ to a transport scattering coefficient $\mu_{s1}'$ for the light having the wavelength $\lambda_1$, and
   p is a predetermined value satisfying $0 \leq p \leq 1$.

8. A method according to claim 1, wherein the arithmetic processing step comprises calculating the concentration of the absorption component in the scattering medium on the basis of a relationship represented by $$V = \ln \frac{I_2(\lambda_1)I_1(\lambda_2)}{I_2(\lambda_2)I_1(\lambda_1)} \times \left[(\varepsilon_2 - \varepsilon_1)\{p\langle L_2(\lambda_2)\rangle + (1-p)\sqrt{k}\langle L_2(\lambda_1)\rangle\} - (\varepsilon_2 - \varepsilon_1)\{q\langle L_1(\lambda_2)\rangle + (1-q)\sqrt{k}\langle L_1(\lambda_1)\rangle\} - \varepsilon_1(1-\sqrt{k})\{\langle L_2(\lambda_1)\rangle + \langle L_1(\lambda_1)\rangle\}\right]^{-1}$$

where
   V is the concentration of the absorption component,
   $\varepsilon_1$ is an absorption coefficient per unit concentration of the absorption component for light having a wavelength $\lambda_1$, $\epsilon_2$ is an absorption coefficient per unit concentration of the absorption component for light having a wavelength $\lambda_2$, $<L_1(\lambda_1)>$ is a mean flight pathlength at a photodetection position $t_1$ for the light having the wavelength $\lambda_1$, $<L_1(\lambda_2)>$ is a mean flight pathlength at the photodetection position $r_1$ for the light having the wavelength $\lambda_2$, $<L_2(\lambda_1)>$ is a mean flight pathlength at a photodetection position $r_2$ for the light having the wavelength $\lambda_1$, $<L_2(\lambda_2)>$ is a mean flight pathlength at the photodetection position $r_2$ for the light having the wavelength $\lambda_2$, $I_1(\lambda_1)$ is a detected light intensity at the photodetection position $r_1$ for light having an incident light intensity $B_1$ and the wavelength $\lambda_1$, $I_1(\lambda_2)$ is a detected light intensity at the photodetection position $r_1$ for light having an incident light intensity $B_2$ and the wavelength $\lambda_2$, $I_2(\lambda_1)$ is a detected light intensity at the photodetection position $r_2$ for the light having the incident light intensity $B_1$ and the wavelength $\lambda_1$, $I_2(\lambda_2)$ is a detected light intensity at the photodetection position $r_2$ for the light having the incident light intensity $B_2$ and the wavelength $\lambda_2$, k is a ratio ($\mu_{s2}'/\mu_{s1}'$) of a transport scattering coefficient $\mu_{s2}'$ for the light having the wavelength $\lambda_2$ to a transport scattering coefficient $\mu_{s1}'$ for the light having the wavelength $\lambda_1$, p is a predetermined value satisfying $0 \leq p \leq 1$, and q is a predetermined value satisfying $0 \leq q \leq 1$.

9. A method according to claim 1, wherein said predetermined relationship is a relationship derived on the basis of an approximate equation represented by $$\frac{\langle L(\mu_{s1}', \mu_a) \rangle}{\langle L(\mu_{s2}', \mu_a) \rangle} = \sqrt{\frac{\mu_{s1}'}{\mu_{s2}'}} \quad \cdots \quad 1 << r\sqrt{3\mu_a\mu_{s1}'}, \quad 1 << r\sqrt{3\mu_a\mu_{s2}'}$$

where $\mu_a$ is an absorption coefficient, $\mu_{s1}'$ is a transport scattering coefficient for the light having the wavelength $\lambda_1$, $\mu_{s2}'$ is a transport scattering coefficient for the light having the wavelength $\lambda_2$, $<L(\mu_{s1}', \mu_a)>$ is a mean flight pathlength for the light having the wavelength $\lambda_1$ (a transport scattering coefficient $\mu_{s1}'$ and an absorption coefficient $\mu_a$), $<L(\mu_{s2}', \mu_a)>$ is a mean flight pathlength for the light having the wavelength $\lambda_2$ (a transport scattering coefficient $\mu_{s2}'$ and an absorption coefficient $\mu_a$), and r>5 mm.

10. A concentration measuring apparatus for an absorption component in a scattering medium, comprising:

a light source for generating at least two light rays having predetermined wavelengths, the light rays having different transport scattering coefficients for a scattering medium as an object to be measured, and a known ratio of the transport scattering coefficients;

light incidence means for making the light rays incident from a light position into the scattering medium;

photodetection means for detecting the light ray which has propagated inside the scattering medium at at least one photodetection position different from the light incident position to acquire at least one photodetection signal;

parameter detection means for detecting, on the basis of the photodetection signal, a light intensity and a mean flight pathlength at the light detection position for each of the at least two light rays having predetermined wavelengths; and arithmetic processing means for calculating a concentration of an absorption component on the basis of a predetermined relationship between the ratio of the transport scattering coefficients, the light intensity, the mean flight pathlength, and a difference between absorption coefficients per unit concentration of the absorption component for the at least two light rays having predetermined wavelengths, said predetermined relationship being a relationship derived on the basis of a fact that a value obtained by partially differentiating a natural logarithm of the detected light intensity by the absorption coefficient equals the mean flight pathlength without neglecting a difference in mean flight pathlength due to the difference in scattering coefficients.

11. An apparatus according to claim 10, wherein each of the at least two light rays having predetermined wavelengths is a pulse light ray.

12. An apparatus according to claim 10, wherein each of the at least two light rays having predetermined wavelengths is a sine-wave-modulated light ray having a predetermined modulation frequency component, the light intensity is calculated from an amplitude of a signal having the predetermined modulation frequency component, which is contained in the photodetection signal, and the mean flight pathlength is calculated from a phase delay of the signal having the predetermined modulation frequency component.

13. An apparatus according to claim 10, wherein each of the at least two light rays having predetermined wavelengths is a sine-wave-modulated light ray having a predetermined modulation frequency component, the light intensity is calculated from a DC component of the photodetection signal, and the mean flight pathlength is calculated from a phase delay of a signal having the predetermined modulation frequency component, which is contained in the photodetection signal.

14. An apparatus according to claim 10, wherein each of the at least two light rays having predetermined wavelengths is a modulated light ray having a predetermined repetitive frequency component, the light intensity is calculated from an amplitude of a signal having the predetermined repetitive modulation frequency component or a frequency component of an integer multiple thereof, which is contained in the photodetection signal, and the mean flight pathlength is calculated from a phase delay of the signal having the predetermined repetitive modulation frequency component or the frequency component of an integer multiple thereof.

15. An apparatus according to claim 10, wherein each of the at least two light rays having predetermined wavelengths is a modulated light ray having a predetermined repetitive frequency component, the light intensity is calculated from a DC component of the photodetection signal, and the mean flight pathlength is calculated from a phase delay of a signal having the predetermined repetitive modulation frequency component or a frequency component of an integer multiple thereof, which is contained in the photodetection signal.

16. An apparatus according to claim 10, wherein the arithmetic processing means calculates the concentration of the absorption component in the scattering medium on the basis of a relationship represented by $$V = \ln \frac{I_1(\lambda_1)B_2}{kI_1(\lambda_2)B_1 \left[(\varepsilon_2 - \varepsilon_1)\{p\langle L_1(\lambda_2)\rangle + (1-p)\sqrt{k}\langle L_1(\lambda_1)\rangle\} - \varepsilon_1(1-\sqrt{k})\langle L_1(\lambda_1)\rangle\right]^{-1}}$$

where

V is the concentration of the absorption component, $\varepsilon_1$ is an absorption coefficient per unit concentration of the absorption component for light having a wavelength $\lambda_1$, $\varepsilon_2$ is an absorption coefficient per unit concentration of the absorption component for light having a wavelength $\lambda_2$, $\langle L_1(\lambda_1)\rangle$ is a mean flight pathlength for the light having the wavelength $\lambda_1$, $\langle L_1(\lambda_2)\rangle$ is a mean flight pathlength for the light having the wavelength $\lambda_2$, $I_1(\lambda_1)$ is a detected light intensity for light having an incident light intensity $B_1$ and the wavelength $\lambda_1$, $I_1(\lambda_2)$ is a detected light intensity for light having an incident light intensity $B_2$ and the wavelength $\lambda_2$, k is a ratio ($\mu_{s2}'/\mu_{s1}'$) of a transport scattering coefficient $\mu_{s2}'$ for the light having the wavelength $\lambda_2$ to a transport scattering coefficient $\mu_{s1}'$ for the light having the wavelength $\lambda_1$, and p is a predetermined value satisfying $0 \leq p \leq 1$.

17. An apparatus according to claim 10, wherein the arithmetic processing means calculates the concentration of the absorption component in the scattering medium on the basis of a relationship represented by $$V = \ln \frac{I_2(\lambda_1)I_1(\lambda_2)}{I_2(\lambda_2)I_1(\lambda_1)} \times \left[(\varepsilon_2 - \varepsilon_1)\{p\langle L_2(\lambda_2)\rangle + (1-p)\sqrt{k}\langle L_2(\lambda_1)\rangle\} - (\varepsilon_2 - \varepsilon_1)\{q\langle L_1(\lambda_2)\rangle + (1-q)\sqrt{k}\langle L_1(\lambda_1)\rangle\} - \varepsilon_1(1-\sqrt{k})\{\langle L_2(\lambda_1)\rangle + \langle L_1(\lambda_1)\rangle\}\right]^{-1}$$

where

V is the concentration of the absorption component, $\varepsilon_1$ is an absorption coefficient per unit concentration of the absorption component for light having a wavelength $\lambda_1$, $\varepsilon_2$ is an absorption coefficient per unit concentration of the absorption component for light having a wavelength $\lambda_2$, $\langle L_1(\lambda_1)\rangle$ is a mean flight pathlength at a photodetection position $r_1$ for the light having the wavelength $\lambda_1$, $\langle L_1(\lambda_2)\rangle$ is a mean flight pathlength at the photodetection position $r_1$ for the light having the wavelength $\lambda_2$, $\langle L_2(\lambda_1)\rangle$ is a mean flight pathlength at a photodetection position $r_2$ for the light having the wavelength $\lambda_1$, $\langle L_2(\lambda_2)\rangle$ is a mean flight pathlength at the photodetection position $r_2$ for the light having the wavelength $\lambda_2$, $I_1(\lambda_1)$ is a detected light intensity at the photodetection position $r_1$ for light having an incident light intensity $B_1$ and the wavelength $\lambda_1$, $I_1(\lambda_2)$ is a detected light intensity at the photodetection position $r_1$ for light having an incident light intensity $B_2$ and the wavelength $\lambda_2$, $I_2(\lambda_1)$ is a detected light intensity at the photodetection position $r_2$ for the light having the incident light intensity $B_1$ and the wavelength $\lambda_1$, $I_2(\lambda_2)$ is a detected light intensity at the photodetection position $r_2$ for the light having the incident light intensity $B_2$ and the wavelength $\lambda_2$, k is a ratio ($\mu_{s2}'/\mu_{s1}'$) of a transport scattering coefficient $\mu_{s2}'$ for the light having the wavelength $\lambda_2$ to a transport scattering coefficient $\mu_{s1}'$ for the light having the wavelength $\lambda_1$, p is a predetermined value satisfying $0 \leq p \leq 1$, and q is a predetermined value satisfying $0 \leq q \leq 1$.

18. An apparatus according to claim 10, wherein said predetermined relationship is a relationship derived on the basis of an approximate equation represented by $$\frac{\langle L(\mu_{s1}', \mu_a)\rangle}{\langle L(\mu_{s2}', \mu_a)\rangle} = \sqrt{\frac{\mu_{s1}'}{\mu_{s2}'}} \quad \cdots \quad 1 << r\sqrt{3\mu_a\mu_{s1}'}, 1 << r\sqrt{3\mu_a\mu_{s2}'}$$

where $\mu_a$ is an absorption coefficient, $\mu_{s1}'$ is a transport scattering coefficient for the light having the wavelength $\lambda_1$, $\mu_{s2}'$ is a transport scattering coefficient for the light having the wavelength $\lambda_2$, $\langle L(\mu_{s1}',\mu_a)\rangle$ is a mean flight pathlength for the light having the wavelength $\lambda_1$ (a transport scattering coefficient $\mu_{s1}'$ and an absorption coefficient $\mu_a$), $\langle L(\mu_{s2}',\mu_a)\rangle$ is a mean flight pathlength for the light having the wavelength $\lambda_2$ (a transport scattering coefficient $\mu_{s2}'$ and an absorption coefficient $\mu_a$), and r>5 mm.

19. A concentration measuring method for an absorption component in a scattering medium, comprising:

a light generation step of generating at least two light rays having predetermined wavelengths, the light rays having different transport scattering coefficients for a scattering medium as an object to be measured, and a known ratio of the transport scattering coefficients;

a light incidence step of making the light rays incident from a light incident position into the scattering medium;

a photodetection step of detecting the light ray which has propagated inside the scattering medium at at least one photodetection position different from the light incident position to acquire at least one photodetection signal;

a parameter detection step of detecting, on the basis of the photodetection signal, a light intensity and a mean flight pathlength at the light detection position for each of the at least two light rays having predetermined wavelengths; and an arithmetic processing step of calculating a concentration of an absorption component on the basis of a predetermined relationship between the ratio of the transport scattering coefficients, the light intensity, the mean flight pathlength, and a difference between absorption coefficients per unit concentration of the absorption component for the at least two light rays having predetermined wavelengths, wherein the arithmetic processing step comprises calculating the concentration of the absorption component in the scattering medium on the basis of a relationship represented by $$V = \ln\frac{I_1(\lambda_1)B_2}{kI_1(\lambda_2)B_1}\left[(\varepsilon_2-\varepsilon_1)\{p\langle L_1(\lambda_2)\rangle + (1-p)\sqrt{k}\,\langle L_1(\lambda_1)\rangle\} - \varepsilon_1(1-\sqrt{k})\langle L_1(\lambda_1)\rangle\right]^{-1}$$

where

V is the concentration of the absorption component, $\epsilon_1$ is an absorption coefficient per unit concentration of the absorption component for light having a wavelength $\lambda_1$, $\epsilon_2$ is an absorption coefficient per unit concentration of the absorption component for light having a wavelength $\lambda_2$, $\langle L_1(\lambda_1)\rangle$ is a mean flight pathlength for the light having the wavelength $\lambda_1$, $\langle L_1(\lambda_2)\rangle$ is a mean flight pathlength for the light having the wavelength $\lambda_2$, $I_1(\lambda_1)$ is a detected light intensity for light having an incident light intensity $B_1$ and the wavelength $\lambda_1$, $I_1(\lambda_2)$ is a detected light intensity for light having an incident light intensity $B_2$ and the wavelength $\lambda_2$, k is a ratio ($\mu_{s2}'/\mu_{s1}'$) of a transport scattering coefficient $\mu_{s2}'$ for the light having the wavelength $\lambda_2$ to a transport scattering coefficient $\mu_{s1}'$ for the light having the wavelength $\lambda_1$, and p is a predetermined value satisfying $0 \leq p \leq 1$.

20. A concentration measuring method for an absorption component in a scattering medium, comprising:

a light generation step of generating at least two light rays having predetermined wavelengths, the light rays having different transport scattering coefficients for a scattering medium as an object to be measured, and a known ratio of the transport scattering coefficients;

a light incidence step of making the light rays incident from a light incident position into the scattering medium;

a photodetection step of detecting the light ray which has propagated inside the scattering medium at at least one photodetection position different from the light incident position to acquire at least one photodetection signal;

a parameter detection step of detecting, on the basis of the photodetection signal, a light intensity and a mean flight pathlength at the light detection position for each of the at least two light rays having predetermined wavelengths; and an arithrnetic processing step of calculating a concentration of an absorption component on the basis of a predetermined relationship between the ratio of the transport scattering coefficients, the light intensity, the mean flight pathlength, and a difference between absorption coefficients per unit concentration of the absorption component for the at least two light rays having predetermined wavelengths, wherein the arithmetic processing step comprises calculating the concentration of the absorption component in the scattering medium on the basis of a relationship represented by $$V = \ln\frac{I_2(\lambda_1)I_1(\lambda_2)}{I_2(\lambda_2)I_1(\lambda_1)} \times \left[(\varepsilon_2-\varepsilon_1)\{p\langle L_2(\lambda_2)\rangle + (1-p)\sqrt{k}\,\langle L_2(\lambda_1)\rangle\} - (\varepsilon_2-\varepsilon_1)\{q\langle L_1(\lambda_2)\rangle + (1-q)\sqrt{k}\,\langle L_1(\lambda_1)\rangle\} - \right.$$

$$\left.\varepsilon_1(1-\sqrt{k})\{\langle L_2(\lambda_1)\rangle + \langle L_1(\lambda_1)\rangle\}\right]^{-1}$$

where

V is the concentration of the absorption component, $\epsilon_1$ is an absorption coefficient per unit concentration of the absorption component for light having a wavelength $\lambda_1$, $\epsilon_2$ is an absorption coefficient per unit concentration of the absorption component for light having a wavelength $\lambda_2$, $\langle L_1(\lambda_1)\rangle$ is a mean flight pathlength at a photodetection position $r_1$ for the light having the wavelength $\lambda_1$, $\langle L_1(\lambda_2)\rangle$ is a mean flight pathlength at the photodetection position $r_1$ for the light having the wavelength $\lambda_2$, $\langle L_2(\lambda_1)\rangle$ is a mean flight pathlength at a photodetection position $r_2$ for the light having the wavelength $\lambda_1$, $\langle L_2(\lambda_2)\rangle$ is a mean flight pathlength at the photodetection position $r_2$ for the light having the wavelength $\lambda_2$, $I_1(\lambda_1)$ is a detected light intensity at the photodetection position $r_1$ for light having an incident light intensity $B_1$ and the wavelength $\lambda_1$, $I_1(\lambda_2)$ is a detected light intensity at the photodetection position $r_1$ for light having an incident light intensity $B_2$ and the wavelength $\lambda_2$, $I_2(\lambda_1)$ is a detected light intensity at the photodetection position $r_2$ for the light having the incident light intensity $B_1$ and the wavelength $\lambda_1$, $I_2(\lambda_2)$ is a detected light intensity at the photodetection position $r_2$ for the light having the incident light intensity $B_2$ and the wavelength $\lambda_2$, k is a ratio ($\mu_{s2}'/\mu_{s1}'$) of a transport scattering coefficient $\mu_{s2}'$ for the light having the wavelength $\lambda_2$ to a transport scattering coefficient $\mu_{s1}'$ for the light having the wavelength $\lambda_1$, p is a predetermined value satisfying $0 \leq p \leq 1$, and q is a predetermined value satisfying $0 \leq q \leq 1$.

21. A concentration measuring apparatus for an absorption component in a scattering medium, comprising:

a light source for generating at least two light rays having predetermined wavelengths, the light rays having different transport scattering coefficients for a scattering medium as an object to be measured, and a known ratio of the transport scattering coefficients;

light incidence means for making the light rays incident from a light position into the scattering medium;

photodetection means for detecting the light ray which has propagated inside the scattering medium at at least one photodetection position different from the light incident position to acquire at least one photodetection signal;

parameter detection means for detecting, on the basis of the photodetection signal, a light intensity and a mean flight pathlength at the light detection position for each of the at least two light rays having predetermined wavelengths; and arithmetic processing means for calculating a concentration of an absorption component on the basis of a predetermined relationship between the ratio of the transport scattering coefficients, the light intensity, the mean flight pathlength, and a difference between absorption coefficients per unit concentration of the absorption component for the at least two light rays having predetermined wavelengths, wherein the arithmetic processing means calculates the concentration of the absorption component in the scattering medium on the basis of a relationship represented by $$V = \ln\frac{I_1(\lambda_1)B_2}{kI_1(\lambda_2)B_1\left[(\varepsilon_2 - \varepsilon_1)\{p\langle L_1(\lambda_2)\rangle + (1-p)\sqrt{k}\,\langle L_1(\lambda_1)\rangle\} - \varepsilon_1(1-\sqrt{k})\langle L_1(\lambda_1)\rangle\right]^{-1}}$$

where

V is the concentration of the absorption component, $\varepsilon_1$ is an absorption coefficient per unit concentration of the absorption component for light having a wavelength $\lambda_1$, $\varepsilon_2$ is an absorption coefficient per unit concentration of the absorption component for light having a wavelength $\lambda_2$, $\langle L_1(\lambda_1)\rangle$ is a mean flight pathlength for the light having the wavelength $\lambda_1$, $\langle L_1(\lambda_2)\rangle$ is a mean flight pathlength for the light having the wavelength $\lambda_2$, $I_1(\lambda_1)$ is a detected light intensity for light having an incident light intensity $B_1$ and the wavelength $\lambda_1$, $I_1(\lambda_2)$ is a detected light intensity for light having an incident light intensity $B_2$ and the wavelength $\lambda_2$, k is a ratio $(\mu_{s2}'/\mu_{s1}')$ of a transport scattering coefficient $\mu_{s2}'$ for the light having the wavelength $\lambda_2$ to a transport scattering coefficient $\mu_{s1}'$ for the light having the wavelength $\lambda_1$, and p is a predetermined value satisfying $0 \leq p \leq 1$.

22. A concentration measuring apparatus for an absorption component in a scattering medium, comprising:

a light source for generating at least two light rays having predetermined wavelengths, the light rays having different transport scattering coefficients for a scattering medium as an object to be measured, and a known ratio of the transport scattering coefficients;

light incidence means for making the light rays incident from a light position into the scattering medium;

photodetection means for detecting the light ray which has propagated inside the scattering medium at at least one photodetection position different from the light incident position to acquire at least one photodetection signal;

parameter detection means for detecting, on the basis of the photodetection signal, a light intensity and a mean flight pathlength at the light detection position for each of the at least two light rays having predetermined wavelengths; and arithmetic processing means for calculating a concentration of an absorption component on the basis of a predetermined relationship between the ratio of the transport scattering coefficients, the light intensity, the mean flight pathlength, and a difference between absorption coefficients per unit concentration of the absorption component for the at least two light rays having predetermined wavelengths, wherein the arithmetic processing means calculates the concentration of the absorption component in the scattering medium on the basis of a relationship represented by $$V = \ln\frac{I_2(\lambda_1)I_1(\lambda_2)}{I_2(\lambda_2)I_1(\lambda_1)} \times \left[(\varepsilon_2 - \varepsilon_1)\{p\langle L_2(\lambda_2)\rangle + (1-p)\sqrt{k}\,\langle L_2(\lambda_1)\rangle\} - (\varepsilon_2 - \varepsilon_1)\{q\langle L_1(\lambda_2)\rangle + (1-q)\sqrt{k}\,\langle L_1(\lambda_1)\rangle\} - \varepsilon_1(1-\sqrt{k})\{\langle L_2(\lambda_1)\rangle + \langle L_1(\lambda_1)\rangle\}\right]^{-1}$$

where

V is the concentration of the absorption component, $\varepsilon_1$ is an absorption coefficient per unit concentration of the absorption component for light having a wavelength $\lambda_1$, $\varepsilon_2$ is an absorption coefficient per unit concentration of the absorption component for light having a wavelength $\lambda_2$, $\langle L_1(\lambda_1)\rangle$ is a mean flight pathlength at a photodetection position $r_1$ for the light having the wavelength $\lambda_1$, $\langle L_1(\lambda_2)\rangle$ is a mean flight pathlength at the photodetection position $r_1$ for the light having the wavelength $\lambda_2$, $\langle L_2(\lambda_1)\rangle$ is a mean flight pathlength at a photodetection position $r_2$ for the light having the wavelength $\lambda_1$, $\langle L_2(\lambda_2)\rangle$ is a mean flight pathlength at the photodetection position $r_2$ for the light having the wavelength $\lambda_2$, $I_1(\lambda_1)$ is a detected light intensity at the photodetection position $r_1$ for light having an incident light intensity $B_1$ and the wavelength $\lambda_1$, $I_1(\lambda_2)$ is a detected light intensity at the photodetection position $r_1$ for light having an incident light intensity $B_2$ and the wavelength $\lambda_2$, $I_2(\lambda_1)$ is a detected light intensity at the photodetection position $r_2$ for the light having the incident light intensity $B_1$ and the wavelength $\lambda_1$, $I_2(\lambda_2)$ is a detected light intensity at the photodetection position $r_2$ for the light having the incident light intensity $B_2$ and the wavelength $\lambda_2$, k is a ratio $(\mu_{s2}'/\mu_{s1}')$ of a transport scattering coefficient $\mu_{s2}'$ for the light having the wavelength $\lambda_2$ to a transport scattering coefficient $\mu_{s1}'$ for the light having the wavelength $\lambda_1$, p is a predetermined value satisfying $0 \leq p \leq 1$, and q is a predetermined value satisfying $0 \leq q \leq 1$.

* * * * *